(12) United States Patent
Herane-Vives et al.

(10) Patent No.: US 11,959,928 B2
(45) Date of Patent: Apr. 16, 2024

(54) METHOD FOR MEASURING AVERAGE CORTISOL AND GLUCOSE CONCENTRATIONS IN EARWAX

(71) Applicant: TREARS LTD., London (GB)

(72) Inventors: Andrés Herane-Vives, London (GB); Jan Benöhr-Riveros, Munich (DE)

(73) Assignee: TREARS LTD., London (GB)

( * ) Notice: Subject to any disclaimer, the term of this patent is extended or adjusted under 35 U.S.C. 154(b) by 253 days.

(21) Appl. No.: 16/957,004

(22) PCT Filed: Dec. 20, 2018

(86) PCT No.: PCT/IB2018/060470
§ 371 (c)(1),
(2) Date: Jun. 22, 2020

(87) PCT Pub. No.: WO2019/123392
PCT Pub. Date: Jun. 27, 2019

(65) Prior Publication Data
US 2020/0333363 A1 Oct. 22, 2020

Related U.S. Application Data

(60) Provisional application No. 62/608,162, filed on Dec. 20, 2017.

(51) Int. Cl.
*G01N 33/74* (2006.01)
*A61B 10/00* (2006.01)
(Continued)

(52) U.S. Cl.
CPC ....... *G01N 33/743* (2013.01); *A61B 10/0045* (2013.01); *G01N 1/04* (2013.01);
(Continued)

(58) Field of Classification Search
CPC .......... G01N 33/743; G01N 1/04; G01N 1/28; G01N 1/286; G01N 1/4055; G01N 5/00;
(Continued)

(56) References Cited

U.S. PATENT DOCUMENTS 4,766,886 A * 8/1988 Juhn ................. A61F 11/202
600/200
2003/0120180 A1* 6/2003 Kaylor .................. A61B 42/20
600/584

FOREIGN PATENT DOCUMENTS

EP 0 184 237 A1 6/1986
EP 0 234 061 A1 9/1987
(Continued)

OTHER PUBLICATIONS

Burkhart C.N., et al., Cerumen Composition by Flash Pyrolysis-Gas Chromatography/Mass Spectometry, Otology and Neurotology 2001 US, vol. 22, No. 6, 2001, pp. 715-722, XP9512234, ISSN: 1531-7129.
(Continued)

*Primary Examiner* — Robert R Raevis
(74) *Attorney, Agent, or Firm* — TechMark Greenstein Law P.C.

(57) ABSTRACT

A method for measuring glucose and cortisol levels in earwax, wherein the measured levels of cortisol and glucose are interpreted as the average cortisol and glucose levels and a medical device that provides an effective, safe and hygienic self-extraction of earwax.

9 Claims, 13 Drawing Sheets

(51) Int. Cl.
*G01N 1/04* (2006.01)
*G01N 1/28* (2006.01)
*G01N 1/40* (2006.01)
*G01N 5/00* (2006.01)
*G01N 21/64* (2006.01)

(52) U.S. Cl.
CPC ............... *G01N 1/28* (2013.01); *G01N 1/286* (2013.01); *G01N 1/4055* (2013.01); *G01N 5/00* (2013.01); *G01N 21/6486* (2013.01); *A61B 2010/0054* (2013.01); *G01N 2001/4061* (2013.01)

(58) Field of Classification Search
CPC ....... G01N 21/6486; G01N 2001/4061; G01N 33/4833; A61B 10/0045; A61B 2010/0054; A61F 11/06
USPC ....... 73/864.71, 866; 435/7.92, 14; 600/300, 600/316, 365, 562, 570, 572
See application file for complete search history.

(56) References Cited

FOREIGN PATENT DOCUMENTS

SU      1 067 459 A1    1/1984
WO     2015/083161 A1    6/2015

OTHER PUBLICATIONS

Trumble, et al: Blue Whale Earplug Reveals Lifetime Of Contaminant Exposure And Hormone Profiles, Proceedings of the National Academy of Sciences of the United States of America, vol. 110, No. 42, Sep. 16, 2013, pp. 1922-16926, XP055575579, US, ISSN: 0027-8424, DOI: 10.1073/pnas.1311418110.
International Search Report and Written Opinion, dated Mar. 29, 2019, International Application No. PCT/IB2018/060470, International Filing Date: Dec. 20, 2018, Earliest Priority Date: Dec. 20, 2017; Inventors/Applicants Andrés Herane-Vives, Jan Benöhr-Riveros.

\* cited by examiner

METHOD FOR MEASURING AVERAGE CORTISOL AND GLUCOSE CONCENTRATIONS IN EARWAX

CROSS-REFERENCE TO RELATED APPLICATIONS

This application is the U.S. national phase of PCT Application No. PCT/IB2018/060470, filed on Dec. 20, 2018, which claims the benefit of U.S. Provisional Application No. 62/608,162, filed on Dec. 20, 2017, the disclosures of which are incorporated in their entirety by reference herein.

BACKGROUND OF THE INVENTION

A. Field of the Invention

The present invention is related with methods for measuring cortisol and glucose concentrations, and more particularly to a method for measuring average cortisol and glucose levels in earwax.

B. Description of the Related Art

1$^{st}$ Problem

A Lack of a Reliable and Innocuous Method for Measuring the Average Concentration of Glucose Levels Chronic diseases account for the largest among of deaths (71%) around the world, and diabetes is the fourth among them (WHO, 2018). Furthermore, according to the same WHO report, 650 million adults suffer from another chronic disease, such as obesity. Even more outrageous it is the figure that indicates that 39% of adults aged 18 years and over is overweight. Unfortunately, this additional widespread chronic disease also shows an upward trend. Indeed, the worldwide prevalence of obesity nearly tripled between 1975 and 2016 (NCD-RisC et al., 2017).

These two epidemic diseases are closely related. Nearly 90% of patients with the most common type of diabetes or type II diabetes is related to excess body weight (Wu et al., 2014). Moreover, they commonly share the same metabolic alteration: increased glucose levels. This finding is required for making the diagnoses of diabetes. Furthermore, subjects with increased glycaemic levels, but not in a diabetic range, also show up to 4.5 odds to be obese (Meigs et al., 1998).

Current measures from "short-term" glucose specimens, such as serum, have significant limitations in the assessment of the average concentration of glucose level. This is because glucose levels vary greatly during the day. Furthermore, day-to-day perturbations during periods of stress (Dagogo-Jack, 2010), smoking (Frati et al., 1996), high blood pressure (Modan et al., 1985), BMI (Hiller et al., 1988) and physical activity (Allen et al., 2009) can affect its levels.

Several glucose measurements, such as during fasting and postprandial glucose concentrations have been standardised with the aim of providing a more accurate glycaemic level. However, taking those lab tests can result quite demanding for patients. Furthermore, they do not accurately reflect the average glycaemic levels, which is the needed level to monitor the long-term glycaemic profile in diabetic patients. Indeed, they usually are found either, below the mean, such as those seen in the Fasting Serum Glucose (FSG) or below that value in the Postprandial Serum Glucose (PSG) (Peter et al., 2006).

Glycated haemoglobin ($HbA_{1c}$); a form of haemoglobin that shows positive correlations with both glycaemic indexes: fasting and postprandial levels is commonly used as an index of the long-term average of glucose levels (Monnier et al., 2006; Bonora et al., 2001; Rohlfing et al., 2002), that is why it is considered the current gold-standard method for reflecting the average glucose concentration. However, in comparison to diabetic patients, healthy people show weaker associations between postprandial and $HbA_{1c}$ and between fasting glycaemic levels and $HbA_{1c}$ (van't Riet et al., 2010). Indeed, a large study showed correlations of 0.46 between FSG and $HbA_{1c}$ and 0.33 between PSG and $HbA_{1c}$ among the general population in comparison to the diabetic population that exhibited 0.71 and 0.79 for the same associations (van't Riet et al., 2010). These results undermine the $HbA_{1c}$ ability to act as a screening test (Dagogo-Jack, 2010). On the other hand, fasting glucose levels shows a stronger association with $HbA_{1c}$ than postprandial glucose levels with the same protein among healthy people and in diabetic patients with poor glycaemic control (Monnier et al., 2006). This means that $HbA_{1c}$ could be found within a normal range in diabetic patients who frequently have dietary transgressions. This certainly diminishes the $HbA_{1c}$ capacity to tightly monitor the mean glucose levels among those patients. Therefore, a more accurate method for reflecting the average concentration of glucose levels may be equally weighted postprandial and fasting glycaemic levels. $HbA_{1c}$ is a protein that is measured to identify the three-month average plasma glucose concentration, but it is more greatly weighted (75%) towards plasma glucose concentrations of the past month (Leow, 2016; Mortensen & Vølund, 1988; Tahara & Shima, 1993). Nonetheless, $HbA_{1c}$ does not provide accurate information over shorter periods, such as following earlier changes in glycaemic control, which is a period that generally requires a tight metabolic control (Goldstein et al., 2004; J. H. Kim et al., 2012; Koenig et al., 1976).

It also has some additional limitations. On the one hand, it is not a precise method considering that some usual variables, such as ageing varies $HbA_{1c}$ concentration (Dagogo-Jack, 2010). On the other hand, some common disorders, such as anaemia (Sundaram et al., 2007) and several hemoglobinopathies (up to 7%) (Weatherall, 2011) can affect its levels. Even working long hours predicted a higher level of $HbA_{1c}$ (Azami et al., 2018). Additionally, it is an expensive and commonly unavailable lab test (Sacks, 2011). Ultimately, it is an indirect approximation to the mean glucose level, since it is a protein, rather than the sugar into question, which is directly measure. Some authors, due to all the aforementioned reasons, even doubt about its validity as a diagnostic test for diabetes mellitus and prediabetes (Dagogo-Jack, 2010).

More recently glycated albumin has been used as an index for intermediate periods over 2-4 weeks, However, notwithstanding the several socio-demographic variables, such as age or BMI (Miyashita et al., 2007) or disorders affecting albumin metabolism such as thyroid dysfunction, nephrotic syndrome, or liver cirrhosis (K. J. Kim & Lee, 2012), make the glycated albumin a quite erratic measure in clinical practice (Huh et al., 2014). Furthermore, so far, it has not been validated as a diagnostic method.

It is also important to highlight, all previous samples, either measuring glycaemic, $HbA_{1c}$ or glycated albumin levels are taking from blood, meaning that they are expensive since qualified workers, such as nurses are needed to take those samples. Furthermore, they may be associated with some side effects, such as bleeding and infections, which are even more frequent and complicated in patients with metabolic alterations, such as diabetes. Nonetheless, and regardless of all disadvantages as mentioned earlier, blood sugar is still being the most requested lab test in the Primary Health Care Centre in several countries (Salinas et al., 2014, Zunic, 2012), also representing the third largest lab cost for health systems (Zunic, 2012). $HbA_{1c}$ is also among the most demanded lab test, and it is believed that it is still unrequested (Salinas et al., 2012). Therefore, there is an unquestionable need for developing not only a more beneficial specimen regarding being capable of obtaining a direct average of glucose concentration over different periods, but also a more economical and innocuous method.

$2^{nd}$ Problem

A Lack of a Reliable and Practical Method for Measuring the Average Concentration of Cortisol Levels Depression is another chronic and epidemic disorder. Its diagnosis is considered less than fully reliable (Lieblich et al., 2015). This may be explained by the large heterogeneity of this syndrome. That is why great effort has been invested in developing an accurate biomarker that may improve the consistency of its diagnosis. Measuring cortisol levels has been its most popular biomarker, because it is the most frequently found neurobiological alteration in this syndrome (Pariante, 2009). However, due to the reactive profile of cortisol secretion, the results of this hormone have been very diverging. Indeed, not only does it have its own strong circadian rhythm (Bhagwagar, 2003; Bhagwagar et al., 2005), but also several common variables, such as food intake (Gibson & Checkley, 1999), nicotine (Steptoe & Ussher, 2006), physical exercise (Hill et al., 2008) and stress levels (Kirschbaum et al., 1993; Sharpley, 2012) can affect its levels. This mean that mostly all current specimens, such as plasma are not the most appropriate for reflecting the average cortisol concentration, which is the needed level to describe the state alteration related to the different types of MDEs.

Not long ago, hair specimen started being used for measuring cortisol levels (Dettenborn et al., 2012). It has been shown that this specimen provides an index of the average cortisol concentration, because it accumulates the hormone without being affected by previous short-term cortisol confounding variables (Short et al., 2016a). However, it also has several limitations. Most of its validation studies have been done comparing Hair Cortisol Concentration (HCC) with single or the aggregation of several daily cortisol samples, without considering the nightly cortisol levels. This may explain why, so far, most correlation coefficients between hair and either single or the aggregation of several saliva samples have been quite modest (D'Anna-Hernandez et al., 2011; Sauvé et al., 2007; van Holland et al., 2012; Xie et al., 2011). In fact, few hair validation studies have properly been conducted. That ideal study may correlate HCC with continuous cortisol levels or with cortisol levels that were collected over day and night. In fact, those studies that associated HCC with 24 h urine collection have shown dissimilar results. While Sauvé et al., (2007) only found a moderate correlation between HCC and 24 h urine cortisol collection, Short et al., (2016b) did not find any significant association.

Ultimately, it may also possible that hair is not as good as it thinks for reflecting the average level of cortisol concentration. For instance, it is not completely clear whether sweat glands, which are indeed affected by acute influences also contribute with some amount of cortisol that is accumulated inside the hair (Sharpley, 2012). What it is clear, however, is that the sebaceous glands that undoubtedly deliver cortisol inside the hair shaft are touched, and therefore, influenced by fine networks of nerve fibres (Okumura, 1967). Furthermore, acute influences may also affect the hair cycle. Indeed, there is accumulating evidence that indicates that neurohormones and neurotransmitters released during the stress response may also significantly influence the hair cycle (Paus et al., 2006, 1997; Botchkarev, 2003). In addition to this, the among of cortisol within hair follicle and, therefore, inside the future hair free segment also depends on local metabolic variables that reflect hair state growth (Terao & Katayama, 2016). This explains why hair protocol suggests cutting this keratinised tissue from the posterior scalp vertex. Indeed, less hair growth variability has been observed in that area (Pragst & Balikova, 2006). This may mean that, although acute cortisol confounding variables may not affect HCC, those local factors could do. It may be possible to argue that, rather than accurately reflecting long-term cortisol systemic levels, hair specimen may better provide an index of the long-term cortisol local levels.

Hair specimen also encounters several practical issues that prevent its widespread clinical use. The area with less hair growth variability, the posterior scalp vertex is, at the same time, the most affected region when people have just started losing their hair. In fact, this type of baldness (type IV) affects up to 40% of men and 10% of women above 40 years old (Hamilton, 1951). Additionally, this figure does not include the large percentage of people that cannot provide the sample only because they do not have the minimum required of length hair (at least one cm that represents the retrospective four weeks of cortisol secretion). In fact, one recent study showed that up to 30% of its sample could not, or were not willing to provide that sample for various reasons, including aesthetic ones (Fischer et al., 2016). Importantly, accurately cutting ±1 mm of hair seems a task impossible to achieve. However, being able to discriminate the average cortisol level between weeks may be extremely important to know for clinicians. Indeed, the antidepressant effect normally starts showing its effect after 3, rather than 4 weeks of treatment (Tanum & Malt, 1996). This means that the real antidepressant effect in terms of long-term cortisol level alterations may be not possible to be accurately described using hair samples. Ultimately, conversely to non-keratinised tissues, its analysis is very slow. Indeed, while analysing one saliva sample could take 4 hours and 20 min, the analysis of one hair sample takes more than 30 hours, meaning almost eight times more. Therefore, it is a highly inefficient process. This may explain why its cost can be up to 44.3% more than analysing one short-term cortisol sample, such as saliva (Bristow, 2017). All aforementioned variables definitely hinder its widespread clinical use.

Some covariates may also affect cortisol levels in hair. The gender, for instance, may vary HCC. Several studies have shown that males have increased HCC than females (Garcia-Leon et al., 2018; Vanaelst et al., 2012). Although the wash-out effect of cortisol, given by external factors, such as UV radiation or the use of cleaning products have been ruled out below the fourth closest cm to the root hair (Dettenborn et al., 2010), it is unknown whether an additional wash-out effect, or, in other words, an effect when the specimen has just emerged from scalp do reduce its cortisol levels. Furthermore, hair studies do not agree with a unique type of cortisol extraction, although a great variability has also been related to this step of the hair cortisol analysis. Indeed, up to 3.5 times more cortisol has been extracted when the specimen has been pulverised, rather than cutting it in small pieces (Davenport et al., 2006). Ultimately, it is not clear whether some cosmetic treatments, such as dying hair also has an effect on HCC (Manenschijn et al., 2011; Sauvé et al., 2007).

3$^{rd}$ Problem

A Lack of an Efficient and Safe Device for Self-Cleaning Outer Ears

Unfortunately, so far, no safe self-cleaning device is as effective as the traditional clinical method for cleaning the outer ear. This means that, regardless of the potential utility of earwax sample for measuring the long-term average of glucose and cortisol levels, its widespread clinical use seems unrealistic. It would be very expensive to extract the same, since, so far, only qualified doctors can safely do it.

Furthermore, although cleaning outer ears is not a medical indication, millions of people practise that dangerous habit on a daily basis. Indeed, cotton swabs, which are the most common method for self-cleaning outer ears (Khan et al., 2017) are, at the same time, the main risk factor for several external ear diseases, such as impacted earwax and bleeding (Ahmed et al., 2014; Nussinovitch et al., 2004).

Hence, considering their potential severe side effects, their effectiveness may not be the sole reason for understanding their popularity. Other hypotheses have also been proposed. It has been said that these apparatuses may have an addictive effect. Indeed, their stimulation of the sensitive fibres that surround the external auditive canal can elicit various pleasurable visceral stimuli. However, their chronic use can trigger a vicious circle, described as "itch-scratch cycle" that tends to auto-perpetuate through the time. Thus, increased use of them cannot only cause increased itching, but also explains their consequential abuse (Mochizuki et al., 2014; Pata et al., 2003). Therefore, alerting people about their potential side effects may be insufficient to reduce their huge demand. They are already a commercial success with high expectations of keep growing at high rates in the main global markets. Only one brand, for instance, reported sales for 189.3 million US$ in 2005 and 204.8 US$ during 2014. Furthermore, a recent market study revealed that their sales has exhibited growth rates of 20% in the USA, 32% in China and 26% in Europe between 2011 and 2017, and it is predicted to grow at rates of 20%, 24% and 19%, respectively for the following five years (Hexa Reports, 2017). Therefore, an efficient and safe alternative to these popular risky devices needs to be developed.

Unfortunately, so far, this has not been possible to accomplish. Currently, several ear cleaning products are commercialised with none or minimum effect. Indeed, one comprehensive systematic review showed that, although some cerumenolytics solutions, such as those containing mineral oils may have some utility, it is not clear which of them can provide that help. Furthermore, so far, no device (mechanic or electric) is as good as the mechanic extraction done by the specialist, or through the use of a syringe (the Reiner-Alexander syringe), that can effectively remove that secretion (Clegg et al., 2010).

1st Solution

Earwax Reflects the Average of Glucose and Cortisol Concentration

Few other biological specimens may provide an average of glucose and cortisol levels. Adipose tissue may be one of them, due to its known features for accumulating substances (Szymczak & Milewicz, 1998). However, taking an adipose biopsy from patients seems extremely unrealistic, since it is not only a risky procedure, but also much more expensive than taking blood samples. However, another more approachable specimen may provide those levels. Earwax is an oily secretion also mainly constitutes by lipids (Inaba et al, 1987). It is secreted by apocrine and sebum glands into the auditory ear canal (Montagna, 1955). This secretion may provide an accurate average of the glucose and cortisol levels because no local or acute influences, given the latter by the effect of nerve fibres affect their concentration. In fact, conversely to the sebaceous glands of the hair follicle, it has been demonstrated that the apocrine and sebum glands of the ear are not innerved (Bende, 1981).

Bees also produce their own wax. The role of honeycombs also suggest that earwax may provide additional advantages over blood samples. On one hand, bees are able to store (accumulate) their sugar (honey) in their honeycombs (Fratini et al., 2016) and, on the other hand, due to its bacteriostatic property, it is not consumed by microorganism (Ghanem, 2011). In fact, this property is also share with the human wax (Stoeckelhuber et al., 2006). Thus, this suggests that earwax may not only be capable of accumulating glucose and cortisol levels over long-periods, but also it may be protected from the epidermal flora. This implies that earwax could be collected from home, because; conversely to blood samples, no special storing or transporting conditions should be needed.

Cortisol and glucose are two highly reactive substances. Measuring their chronic levels is a crucial need because they are altered in epidemic disorders. However, so far, biological specimens can only measure their levels for short periods, or with samples that, even though capable of accumulating them for longer periods; their widespread clinical use is unfeasible or expensive. Earwax may be a fairly viable sample with the capacity of accumulating these substances for long periods. However, it is unknown whether that secretion accumulates those reactive substances for long-periods.

Therefore, applicant developed a method of analysis for detecting glucose and cortisol using earwax.

A systematic review evaluated the method of the present invention and a pilot study assessed the efficiency of earwax analysis and whether glucose and cortisol can be detected in a novel specimen. Finally, the effectiveness of several types of sponges for removing artificial wax from one pigskin were also tested Results: Cortisol levels have not been previously measured in earwax. Cortisol and glucose are detected in that oily secretion. The time needed for analysis earwax cortisol was much less than the time needed for analysing the same substance using hair. One cellulose sponge with particular abrasive and absorptive features was the most efficient for removing wax from one piece of a pigskin.

Conclusion: Earwax may constitute the most accurate and efficient specimen for measuring long-term cortisol and glucose levels. A cellulose sponge may be an effective, economical and safe material for its extraction.

2nd Solution

Designing a Safe and Effective Device for Self-Cleaning Ears

In view of the above referred problems, applicant developed a medical device that provides an effective, safe and hygienic self-extraction of earwax.

Furthermore, the device for self-extraction of earwax of the present invention is capable to provide a suitable specimen for the method of analysis for detecting glucose and cortisol using earwax.

SUMMARY OF THE INVENTION

It is therefore a main object of the present invention to provide a method for measuring glucose and cortisol levels in earwax.

It is another main object of the present invention, to provide a novel medical device that provides an effective, safe and hygienic self-extraction of earwax.

These and other objects and advantages of the method for measuring glucose and cortisol levels in earwax and medical device of the present invention will become apparent to those persons having an ordinary skill in the art, from the following detailed description of the embodiments of the invention which will be made with reference to the accompanying drawings.

DETAILED DESCRIPTION OF THE INVENTION

Figure 1:
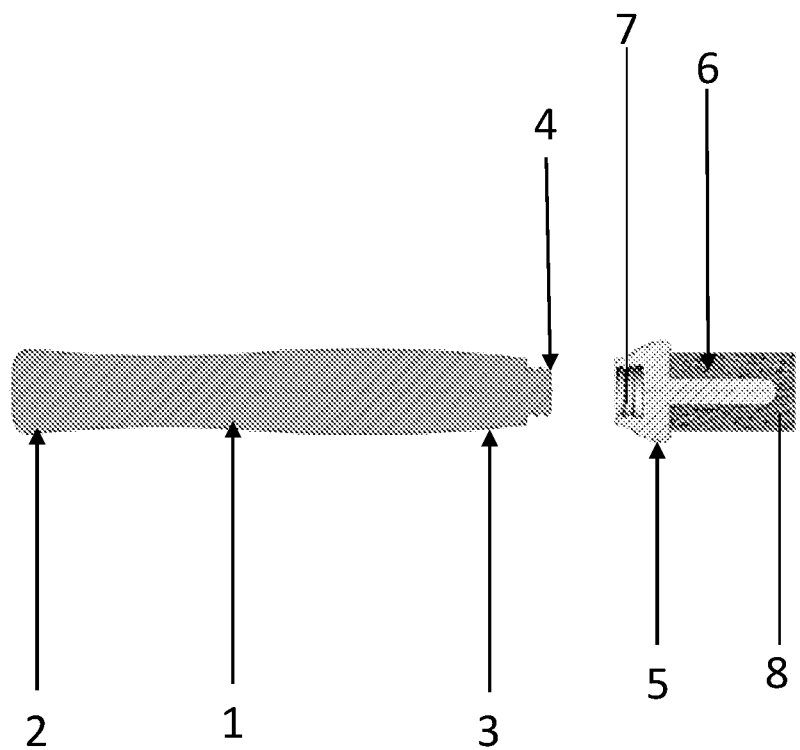
FIG. 1 is a left side view of a first embodiment of the medical device of the present invention showing the cross section of the tip including the sponge.
Figure 2:
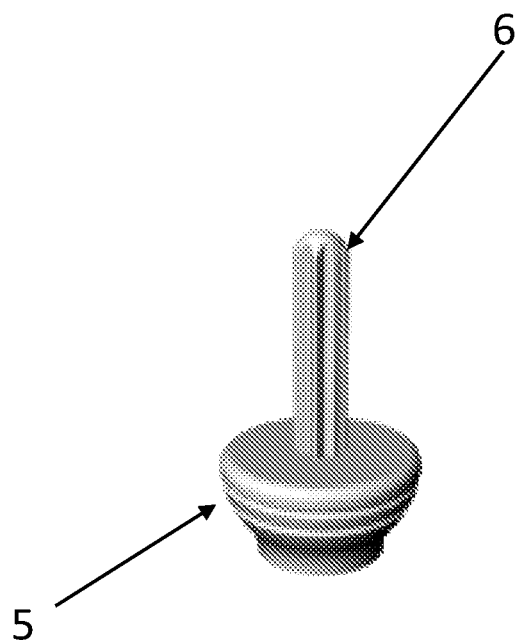
FIG. 2 is a perspective view of the tip of the medical device of the present invention without the sponge.
Figure 3:
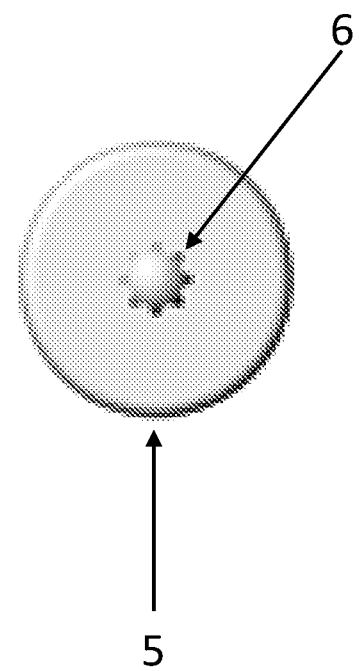
FIG. 3 is an upper view of the tip of the medical device of the present invention without the sponge.
Figure 4:
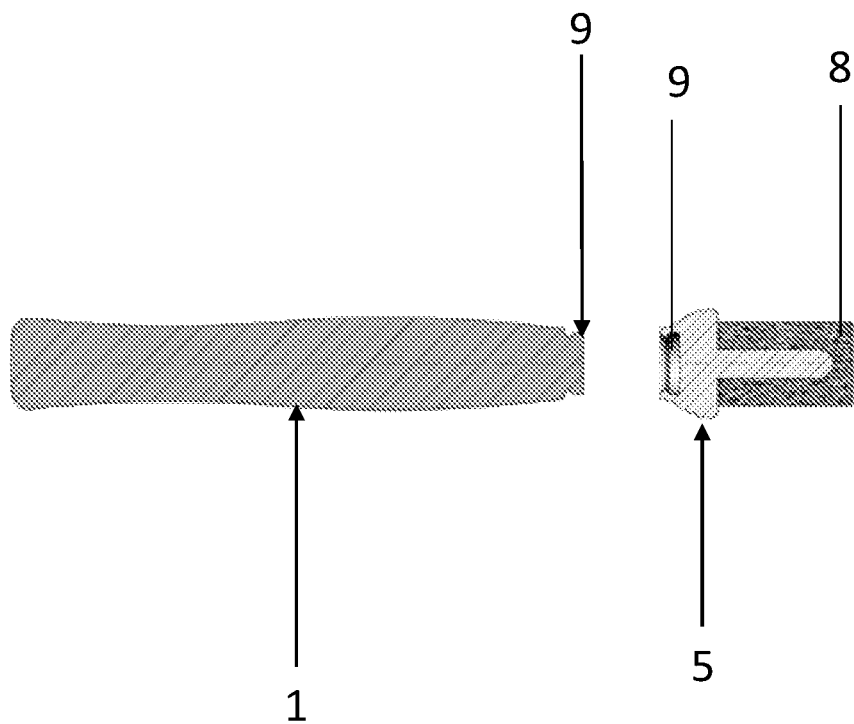
FIG. 4 is a left side view of a second embodiment of the medical device of the present invention showing the cross section of the tip including the sponge.

The method for measuring long-term glucose and cortisol levels in earwax of the present invention will be described in accordance with a preferred embodiment thereof, wherein in its most general embodiment, the method of the present invention comprises:

extracting earwax samples from the ear by any suitable means. The minimum amount of earwax needed for measuring the average cortisol and glucose levels is 0.8 mg;

preparing samples of earwax for the measurement of cortisol and glucose levels in accordance with the measurement means or methods;

measuring cortisol and glucose using any known means or methods wherein the levels of cortisol and glucose are interpreted as the average cortisol and glucose levels.

The extraction of the earwax samples may be carried out by traditional means, for example using a Reiner-Alexander syringe or by using any suitable extraction device.

The preparation of the samples may be carried out in different ways depending on the method for measuring cortisol and glucose to be used. The samples may comprise pure and dry earwax. Their glucose and cortisol analyses may be conducted in different manners, such using immunohistochemistry or ELISA.

In a first specific embodiment of the present invention, the earwax is obtained by using a Reiner-Alexander syringe, from outer ears.

In such first specific embodiment the preparation of the samples and the measurement of the cortisol and glucose levels is carried out as follows:

Preparation of Samples

Cortisol Extraction a) drying the earwax samples by means of a $N_2$ steam at ambient temperature, until all the water is evaporated from the sample. This step can also be done using lyophilization;

b) weighting the dry earwax samples which allow to normalize the amount of cortisol by dry weight. Normalizing means that the measured weight is adjusted to a common scale in order to be able to compare the data;

c) homogenizing the dry samples with 1 ml of Phosphate Buffered Saline (PBS) solution in order to obtain a solution of earwax in PBS. The quantity of Phosphate Buffered Saline (PBS) solution may be of 10 volumes by weight of cerumen, for example, for 100 g of cerumen there are used 1000 ul of Phosphate Buffered Saline (PBS) solution. Furthermore, any hydrophilic solvent may be used such as with physiological serum;

d) dividing the solution obtained in step c) in a first solution portion, and a second solution portion and adding each solution portion to a respective tube;

e) adding 0.5 ml of diethyl-ether to the first solution portion in order to obtain a solution of earwax in PBS mixed with 0.5 mg of diethyl-ether; since the relation between both substances is 1:1. However other suitable families of substances may be also used.

f) agitating the tube containing the solution obtained in step e) during a period of time of at least one minute in order to mix the solution obtained in step f) and adding 0.5 mg of diethyl-ether after resuspending, the relation with PBS being 1:1;

g) cooling the mixed solution obtained in step g) at a temperature of −18 to −21° C., preferably −20° C. during a period of time of at least two hours in order to be sure that the liquid part is frozen and it does not contaminate the organic fraction. This step allows extracting those compounds which are specifically solubilised in diethyl-ether, like cortisol. This is because while the diethyl-ether fraction remains liquid at −20° C., the phosphate fraction freezes;

h) extracting from the cooled solution the compounds which are specifically solubilized in diethyl-ether;

i) drying the remaining fraction of liquid solution using the displacement method with N2. However, other methods can also be using such as evaporation;

j) storing the dried fraction obtained in step i) at −80° C. for further use;

k) adding 300 pg of cortisol to the second solution portion in order to obtain a solution of earwax in PBS mixed with cortisol;

l) adding 0.5 ml of diethyl-ether to the solution obtained in step k) in order to quantify the amount of purified cortisol as a way to assess the efficiency extraction method;

m) agitating the tube containing the solution obtained in step l) during a period of time of at least one minute in order to mix the solution obtained in step m) and adding 0.5 mg of diethyl-ether after resuspending, the relation with PBS being 1:1;

n) cooling the mixed solution obtained in step m) at a temperature of −18 to −21° C., preferably −20° C. during a period of time of at least two hours in order to be sure that the liquid part is frozen, and it does not contaminate the organic fraction;

o) extracting from the cooled solution the compounds which are specifically solubilized in diethyl-ether;

p) drying the remaining fraction of liquid solution using again the displacement method with N2;

q) storing the dried fraction obtained in step i) at −80° C. for further use;

r) in a 3rd tube—without the presence of homogenised solution—0.5 ml of 300 pg/ml of purified cortisol solution was dissolved in PBS at pH 7. This step was done in a bid to obtain the efficiency of cortisol extraction ear-wax protocol.

s) carrying out the same procedure used for the first solution portion and for the second solution portion to extract cortisol from it.

Cortisol Quantification

ELISA techniques are used, according to the manufacturer's instructions (Enzo Life Sciences, Farmingdale, NY) to quantify the amount of cortisol concentration in ear-wax specimens, wherein the quantification of cortisol is carried out as follows:

a) reconstituting the extracted samples using a buffer assay given by the manufacturer, which allows the quantification of cortisol, using colorimetric competitive ELISA techniques, by: adding the buffer to the extracted samples for obtaining a solution, letting the solution rest for 20 minutes However, other range of time can also be used. 20 min of time were enough for rehydrating the solution to an easier resuspension of the buffer. Thereafter the solution was agitated during a period of time of 1 minute to homogenizer the solution. For the purpose of this application buffer is understood as a stable solution because it maintains its Ph within a range regardless a base or acid is added.

b) using a standardized curve for cortisol levels—microplate reader (NovoStar)—to measure the total amount of cortisol in the specimen;

c) normalizing the quantified amount by dry grams of ear-wax using fluorometric techniques in which the fluorometer is excited within a range of 530-570 nm and read within a range of emission of 590-600 nm. Since several variables, such as age, gender, different medical condition and stress levels may affect cortisol levels in ear-wax, it is used, the level of cholesterol, which is not affected by the aforementioned variables avoiding then confusing cortisol results by previous covariates.

Glucose Quantification

A fraction of the previously dissolved ear-wax solution in PBS for measuring cortisol levels is used for measuring glucose levels wherein the quantification of glucose is carried out as follows:

a) measuring glucose levels using the Kit SERA-PAK PLUS (Bayer HealthCare) for glucose levels from the dissolved ear-wax solution, following manufacturer instructions. Glucose absorptions is quantified in triplicate at 505 nm. Glucose concentration (mg/dl) is obtained using its absorption averages, and the total amount of glucose in the dissolved solution is calculated according to the initial weight of the samples after a process of normalization.

In a second specific embodiment of the invention, the earwax is obtained by means of the extraction device of the present invention which comprises:

a handle (1) having a first end (2) and a second end (3), said second end (3) having coupling means which in a preferred embodiment of the invention may comprise a thread (4);

a detachable head (tip) comprising a base (5) and a longitudinally extending elongated sponge holder (6) directly depending from an upper portion of the base, wherein the lower portion of the base has a housing including an internal threaded pattern (7) for receiving the thread (4) of the handle (1), and wherein the sponge holder (6) has a star shaped cross section;

an elongated sponge (8) having a centrally located longitudinal housing (not shown) having a star shaped cross section for receiving the sponge holder (6) of the base (5).

The handle (1) and the base (5) may include any suitable coupling means for coupling the handle, such as a snap joint (9).

The sponge (8) may be made preferable of cellulose and is glued to the sponge holder (6) using a non-allergenic glue.

As previously described, the sponge holder (6) has a star shaped cross section, which improves the earwax extraction while rubbing the sponge (8) inside the ear, however, its cross section may have any suitable shape.

The base (5) is wider than the handle (1), and acts as a safety brake which hinders to introduce the tip inside the ear canal.

The handle (1) is characterised by having a rotationally symmetric form, which allows the user to rub the sponge inside the ear by rotating it inside the outer ear canal.

The sponge (8) is packaged and sealed in wet condition to keep it soft. The used moistener is magnesium chloride ($MgCl_2$), which acts as an antimicrobial agent to prevent microorganism growth during storage shelf-life. The magnesium chloride not only prevents the sponge from growing microorganism but is also supports the extraction of earwax. Furthermore, it has also been used for treating dermatitis (Zhai et al., 1999), the most common side-effect due to the use of cotton swabs (Ahmed et al., 2014). Other known antimicrobial agents may be used.

The earwax is obtained by inserting the tip with the sponge (8) in the ear and rotating the sponge (8) inside the ear canal for around 30 to 60 seconds.

In the second embodiment of the invention, the preparation of the sample is carried out by adding 500 µl of a PBS buffer solution to a 5 ml tube. The sponge was separated from its plastic support and introduced into the tube. After the sponge absorbed the entire solution, the sponge was repeatedly squeezed and absorbed for a period of 2 minutes or as necessary, and then the sponge was squeezed dry and removed from the tube. Subsequently, the resulting solution was dried by displacement with $N_2$ and the resulting content was resuspended in 500 µl of ultrapure water. The resulting solution in the tube was stored at 4° C. until further use, however the solution may be cooled at other suitable range of temperatures. It will be obvious to a person skilled in the art that other amounts of PBS may be used. The proportion between weight and volume is normally 1:2 that it is why 500 µl was used.

In this second specific embodiment, the cortisol levels are measured by means of ELISA techniques and the glucose levels are measured by means of using the Kit SERA-PAK PLUS (Bayer HealthCare) for glucose levels from the dissolved ear-wax solution, following manufacturer instructions. Other suitable and known methods may be used, such as liquid chromatography tandem mass spectrometry (LC—MS/MS).

Pilot Study

Earwax Extraction

Volunteer ears were cleaned using a Reiner-Alexander syringe, because, so far, it is the unique safe method for effectively removing earwax from outer ears (Clegg et al., 2010). That syringe is the traditional method used by ear-nose and throat specialist doctors for removing impacted earwax. Before cleaning both ears, the external auditory canal was examined using an otoscope to rule out the presence of any external ear pathology, such as impacted earwax or perforated eardrum. Briefly, the Reiner-Alexander syringe slowly injects water at 37 Celsius degrees inside the external ear canal. The process of syringing creates a sensation of mild pressure in the ear as the warm water from the syringe flushes the wax out. The expelled water and the volume of extracted earwax were collected in a kidney basin.

Analyses of Cortisol and Glucose Using Earwax Specimen

The cortisol was extracted in accordance with the first specific embodiment of the invention. Also, the cortisol and glucose quantification was performed in accordance with the first specific embodiment of the invention.

The following pilot study was conducted in a group of healthy participants to standardize the cortisol and glucose extraction protocol for earwax specimens.

Glucose and Cortisol Results Using Earwax Specimen (Table 1)

TABLE II.1

Pilot study of cortisol and glucose analyses using samples of human earwax of five Volunteers (Volunteers 0-4).

| Sample | Total pg. of cortisol in the sample | Dried secretion of cortisol (pg./mg) | Glucose measurement (mg/dl) | Total mg of glucose in the sample | Dried secretion of glucose (mg/mg) |
|---|---|---|---|---|---|
| VOLUNTEER 0 | 7251.7 | 127.0 | 16.3 | 815.0 | 14.3 |
| VOLUNTEER 1 | 4917.6 | 111.8 | 38.5 | 1925.0 | 43.8 |
| VOLUNTEER 2 | 3450.8 | 862.7 | 3.6 | 180.0 | 45.0 |
| VOLUNTEER 3 | 3978.3 | 180.8 | 5.4 | 270.0 | 12.3 |
| VOLUNTEER 4 | 3279.8 | 489.5 | 4.2 | 210.0 | 31.3 |
| VOLUNTEER 1 + 15000 pg. CORTISOL | 23564.6 | | | | |
| VOLUNTEER 1 + 300 pg. CORTISOL | 5199.3 | | | | |
| VOLUNTEER 2 + 300 pg. CORTISOL | 3765.3 | | | | |
| VOLUNTEER 3 + 300 pg. CORTISOL | 4249.1 | | | | |

The Effectiveness of Cortisol Extraction and Quantification Protocol in Earwax Specimen in Comparison to Plasma Specimen As previously explained, cortisol extraction effectiveness was controlled dissolving 0.5 ml of 300 pg./ml of purified cortisol solution in PBS at pH 7 and performing the same extraction protocol used in earwax. Results showed an average 281.48±5.16 pg./ml of cortisol concentration, corresponding to the average of cortisol concentration of the 3 tubes (289.2 pg./ml, 273.42 pg./ml and 281.6 pg./ml). This provides 93.8±1.72% of extraction effectiveness, which indicates high effectiveness of the cortisol extraction protocol in earwax specimens The effectiveness of the extraction procedure was also assessed by adding 300 pg. of purified cortisol in the earwax dissolved homogenate solution before addition of diethyl-ether (see methods). This was done in a bid to determine if earwax components do not interfere with cortisol purification. Results are shown in table 2, showing an average of 99.3% recovery rate of purified cortisol from earwax wax homogenates, confirming the high effectiveness of the earwax protocol for measuring cortisol levels.

TABLE II.2

Recuperation rate of cortisol levels in earwax samples

|  | Dried weight of extracted earwax(pg./mg) | Recuperation rate (%) of 300 pg. of added cortisol |
|---|---|---|
| VOLUNTEER 0 | 127.0 | 108.7% |
| VOLUNTEER 1 | 44.0 | 94.0% |
| VOLUNTEER 2 | 4.0 | 105.0% |
| VOLUNTEER 3 | 22.0 | 90.0% |
| VOLUNTEER 4 | 6.7 | 99.0% |

The measurement procedure was also assessed by using three serum samples (participants 0-2) of one previous project, which acted as a control group (Table 3). It was confirmed that the earwax protocol for measuring cortisol levels is indeed reliable because when cortisol levels were again measured using the same serum samples but using the current earwax protocol, the results were almost the same (compare column 3 and 4 in table 3).

TABLE II.3

Serum cortisol levels of three participants (control group)

| Sample | Total pg. of cortisol in the sample | Original levels of serum cortisol levels (ng/ml) | Same serum samples but using the current earwax protocol for measuring cortisol levels (ng/ml) |
|---|---|---|---|
| PARTICIPANT 0 | 73364.9 | 70.5 | 71.3 |
| PARTICIPANT 1 | 153712.6 | 147.8 | 139.1 |
| PARTICIPANT 2 | 79258.5 | 76.2 | 65.4 |

Finally, it can be seen after comparing tables II.4 and table II.5 that earwax cortisol and glucose analyses after using the Alexander-Reiner syringe was faster than measuring cortisol levels in hair.

TABLE II.4

Time needed for analysing cortisol and glucose using earwax samples after using the Alexander-Reiner syringe

|  | Quantification of the analysis time in hours and minutes | |
|---|---|---|
| PROCDEURE | Cortisol in ear washing ears | Glucose in ear washing |
| Centrifugation of the sample | 00:00 | 00:00 |
| Drying of the sample with N2 prior to extraction | 08:30 | 08:30 |
| Extraction of the sample with organic solvent | 02:10 | 02:10 |
| drying of the sample after extraction | 00:40 | 00:40 |
| quantification protocol | 04:00 | 01:00 |
| TOTAL TIME | 15:20 | 12.20 |

TABLE II.5

Time needed and the associated costs for analysing hair cortisol in relation to the same parameters for analysing one sample of salivary

| Biological Sample | | | Saliva cortisol ⁕ | Hair cortisol ⁕ |
|---|---|---|---|---|
| Cost (by unit) ᵟ | Cost (pounds) | | £27.3 | £64.51 |
| Time (hours) | | | | |
|  | Processing Time (hours) | | | |
|  |  | Technical Time | 0 | 0:26 |
|  |  | incubation | 0 | 24:00 |
|  |  | Rotating evaporator Time | 0 | 3:00 |
|  |  | Total, Processing Time | 0 | 27:26 |
|  | Time of Analysis (hours) | | | |
|  |  | Technical time (Hours) | 0:05 | 0:06 |
|  |  | Centrifugation | 0:25 | 0:25 |
|  |  | Robot Time | 4:00 | 4:00 |
|  |  | Total, analysis | 4:30 | 4:31 |
| Total Time (hours) | Processing + Analysis | | 4:30 | 31:57 |

⁕ These values were obtained thanks to the courtesy of Bristow, M. BIOMARKER ANALYSIS LABORATORY QUOTATION AT ANGLIA RUSKIN ENTERPRISE (2017), Cambridge.

However, it can also be seen from table II.4 that, when the Alexander-Reiner syringe is used earwax samples need to be dried before analysing their glucose and cortisol levels, much increasing the total time needed for analysing these samples. Therefore, the device of the present invention should also remove earwax without the mechanism of syringing any solution.

Conclusion

The results of this pilot study showed that levels of glucose and cortisol are detectable in human earwax samples. The time needed for analysing earwax cortisol was significantly less than the time needed for analysing hair cortisol. It was also found that the most appropriate sponge for removing artificial wax was made of cellulose.

Validation Study

Method

Participants were predominantly recruited from staff and student volunteers of Universidad Catolica del Norte (UCN) in Coquimbo, Chile and from its catchment area. All participants were assessed by the same clinical researcher. The sample comprised thirty-seven healthy participants; 20 were female, the mean age was 29.9 years, and the mean BMI was 25.6 kg/m².

All participants were recruited during southern hemisphere winter (between $6^{th}$ of July and $3^{rd}$ of August, 2018). It has previously been found that seasons vary the triglyceride composition of earwax (Cipriani et al., 1990). There were excluded Asian people and people with mental retardation, due to their different earwax characteristics regarding composition and quantity, respectively (Cipriani et al., 1990; Crandell & Roeser, 1993). Participants did not report current or during the previous month history of medical illnesses, including ear pathologies, such as impacted earwax, perforated eardrum or otitis and metabolic illness, such as diabetes and glucose or lactose intolerance. Participants were selected to be free from any medication for at least one month. Subjects were also excluded if they reported, during the previous month any illicit substance use or were exposed to any severe stressor, according to the DMS-III definition (Pichot, 1986).

The validation study had two interviews that were conducted one month apart. A baseline (day=1) and a follow-up (day=30) visit. During the baseline assessment, participants had a comprehensive clinical interview with the purpose of rule out the presence of any medical illness, such as ear pathologies, metabolic illnesses or psychiatric conditions. Socio demographic data were also recorded during that assessment. Once participants were included in the study, their ears were cleaned using the Reiner-Alexander syringe, because, so far, it is the unique safe method for effectively removing earwax from outer ears (Clegg et al., 2010). That syringe is the traditional method used by ear-nose and throat specialist doctors for removing impacted earwax. Participants were instructed to avoid using cotton swabs or the use of any ear cleaning method during the follow-up period. That allowed the applicant to collect a standardised among of earwax secretion thirty days after (the follow-up assessment). 3-8 mg of earwax represent four weeks of earwax production (Cipriani et al., 1986).

The comparable amount of earwax secretion between the right and the left ear side (Cipriani al., 1986) also allowed to design a prospective case-control, rather than a prospective cross-sectional research study. Therefore, during the follow-up assessment, the left ear was cleaned using the Reiner-Alexander syringe [controls] and the right one using the extraction device of the present invention. The self-assessment of some environmental factors, such as the frequency and severity of the most common day-to-day environmental disturbances, using the Hassles Scale (Kanner & Coyne, 1981), and more unexpected environmental factors, such as significant life events, using the Recent Life Changes Questionnaire (RLCQ; Miller & Rahe, 1997) were evaluated during the month prior to study enrolment. Participants also assessed their stress perception during the last month using the Perceived Stress Scale (PSS; Cohen, 1994). All psychometric tools were validated Spanish versions. Ultimately, a standardised satisfaction survey was administrated for evaluating participants' experience using the device of the present invention. That assessment was made using attitude scale construction techniques for summated (Likert) rating scales of 5 points (Spector, 1985). Some categorical and continuous variables, such as their previous participants' knowledge or their frequency of use of cotton swabs were also recorded in that survey. Anthropometric variables, such as weight, height, Body Mass Index (BMI) and waist circumference were also detailed during that visit.

General Results: Socio Demographic, Anthropometric and Self-Administrated Questionnaire Results Results

TABLE III.1

Socio demographic and anthropometric variables

| Variable | | Results |
|---|---|---|
| N: Female | | 20; |
| (%) | | (54.1) |
| Age (Years), | | 29.9, |
| Mean (SD) | | (1.4) |
| Civil status: single (yes), | | 32; |
| N (%) | | (86.5) |
| Under or postgraduate studies | | 16; |
| N, (%) | | (43.2) |
| Ethnicity | Mixed race, | 36, |
| | n (%) | (96.3) |
| | Asian background | 0, |
| | n (%) | (0) |
| Alcohol | (yes)[δ], | 10, |
| | n (%) | (27.0) |
| | Units φ | 1.3; |
| | mean, (SD) | (0.5) |
| Tobacco (yes), | | 9, |
| n (%) | | (24.3) |
| Contraceptive pill (yes), | | 9, |
| n (%) | | (52.9) |
| Mental retardation | | 0; |
| Mean (SD) | | (0) |
| Medical or psychiatric comorbidity, | | 0, |
| n (%) | | (0) |
| Hair washing frequency | | 4.9, |
| (week) | | (0.3) |
| Cosmetic treatment [Ω], | | 1, |
| n (%) yes | | (2.7) |
| Medication[&], | | 0, |
| n (%) | | (0) |

[δ]at least one unit last week
[&]any medication, including psychotropic and steroidal medication.
φ: One alcohol unit is measured as 10 ml or 8 g of pure alcohol. This equals one 25 ml single measure of whisky (Alcohol by volume [ABV] 40%), or a third of a pint of beer (ABV 5-6%) or half a standard (175 ml) glass of red wine (ABV 12%).
[Ω] dyeing, bleaching, permanent straightening or waving.

TABLE III.2

Anthropometric results

| Variable | | Q1 | Median | Mean, (SD) | Q3 |
|---|---|---|---|---|---|
| Height (cm) | Whole sample | 160 | 167 | 166.7, (1.4) | 173 |
| Mean, (SD) | Female | 157 | 160 | 161.6 (1.8) | 166 |
| | Male | 168 | 173 | 172.7, (1.3) | 176 |

TABLE III.2-continued

Anthropometric results

| Variable | | Q1 | Median | Mean, (SD) | Q3 |
|---|---|---|---|---|---|
| Weight (kg) Mean, (SD) | Whole sample | 62 | 72 | 72.5, (2.5) | 78 |
| | Female | 57.5 | 65.5 | 64.6, (2.0) | 72 |
| | Male | 72 | 75 | 81.8, (3.9) | 95 |
| BMI (Kg/m$^2$), Mean (SD) | Whole sample | 23.3 | 24.9 | 25.6, (0.6) | 26.7 |
| | Female | 22.8 | 24.6 | 24.2, (0.6) | 25.5 |
| | Male | 24.1 | 25.4 | 27.2, (1.1) | 31.2 |
| Waist circumference (cm), Mean (SD) | Whole sample | 77 | 86 | 85.9, (2.4) | 95 |
| | Female | 70.5 | 78 | 78.8, (2.3) | 87 |
| | Male | 88 | 93 | 94.4, (3.4) | 102 |

BMI: Body Mass Index.

TABLE III.3

Self-administrated questionnaire results

| Questionnaire | Results |
|---|---|
| Perceived Stress Scale (PSS), Mean (SD) | 22.6, (1.1) |
| Life events score (RLCQ), Mean (SD) | 141.2, (20.8) |
| History of severe life events (RLCQ) (last month), N (%) | 10, (27.0) |
| Number of Hassles (last month), Mean (SD) | 16.7, (1.7) |
| Severity index of hassles, Mean (SD) | 22.9, (2.8) |
| Subjects under increased number (>25) of hassles (last month), N (%) | 9; (24.3) |
| Subjects having problems dealing with their hassles (last month), N (%) | 1, (2.7) |

RLCQ; Recent Life Change Questionnaire,
PSS: Perceived Stress Scale

Overall, it can be said from the tables III.1, III.2 and III.3 that participants comprised a quite homogenous young sample, mainly constituted by females (54.1%). It was also a healthy group of people, in terms of anthropometric variables. However, this group of participants were exposed to an increased number, and more severe hassles and life events than other Chilean control samples (Herane-Vives et al., 2018). This explains, perhaps why their stress perception was higher than other samples of healthy Latins (in Cohen, 1994).

Evaluation of the Extraction Device of the Present Invention (Trears©)

Background: So far, no safe self-cleaning device is as effective as the traditional clinical method for removing earwax. One as such may replace the risky cotton swabs. In this study, we assessed the effectivity and user experience of an original safe self-cleaning outer ear device (Trears).

Methods: The weight of 37 right earwax samples using Trears were compared with the weight of the same number of left earwax samples that were collected using the traditional clinical method (the Reiner-Alexander syringe). The samples represented the retrospective month of earwax secretion. Participants also assessed their self-cleaning ear device experience using a standardised satisfaction survey.

Results: Trears was significantly more effective than the use of the Reiner-Alexander syringe for removing earwax ($p<0.001$). Trears tips with 50% (105.1 μl) of humidity were more effective than Trears with 12.5% (30 μl) for removing earwax ($p<0.05$). Participants considered that its use was safer and more comfortable than the use of cotton swabs.

Conclusion: Trears may constitute a more economical, convenient and efficient method for self-cleaning outer ears in healthy people. This device may also replace the use of the current risky cotton swabs.

The results of the previous pilot study confirmed that one specific abrasive and absorptive sponge was very effective for removing artificial wax from one animal's skin (Herane-Vives & Benohr, 2018). However, its usefulness has not yet been tested in earwax. In this prospective case-control study design, the effectivity and safety of the extraction device of the present invention (Trears) that incorporates that sponge in healthy participants was tested.

Earwax Samples

The clinical research assistant was explicitly trained in the use of the Reiner-Alexander syringe by one ear-nose-throat specialist doctor on 30th of May 2018. Before cleaning both ears, the external auditory canal was examined using an otoscope to rule out the presence of any external ear pathology, such as impacted earwax or perforated eardrum. Briefly, the Reiner-Alexander syringe slowly injects water at 37 Celsius degrees inside the external ear canal. The process of syringing creates a sensation of mild pressure in the ear as the warm water from the syringe flushes the wax out. The expelled water and the volume of extracted earwax were collected in a kidney basin. During the follow-up visit, participants self-cleaned their right ear using Trears, according to the manufacturer instructions (Diagram 1).

The disposable tip sponges were previously moisted with different levels of humidity using Magnesium Chloride (MgCl2). The magnesium oil used during the study was a 31% magnesium chloride solution in aqua, which is also used for massages, skin regeneration and care. Due to its high magnesium content the solution has a smooth, nurturing and fluid texture. It contains no oil in nature, but has a silky feeling like oil. Each millilitre of magnesium oil contained about 103 mg elementary magnesium. Four earwax samples were labelled, weighted and store at minus. All earwax samples were labelled, weighted and store at 4 degree Celsius.

Statistical Analysis

The data were checked for normality using the Kolmogorov-Smirnov statistical test and graphics methods, such as histograms. Apart from the follow-up left samples ($p=0.03$), all other values were normally distributed (all $p>0.05$). Therefore, we used repeated t-tests for comparing the amount of extracted earwax volume between left and right ear of the baseline extractions and between the baseline and follow-up extraction. Wilcoxon matched-pairs signed-ranks test was used for comparing the amount of extracted earwax between the left and right ear follow-up extractions. Linear regression analysis was used to determine the association between the volume of extracted earwax by Trears and different biological variables, or between the same volume and customer satisfaction survey questions. The level of significance was set at $p \leq 0.05$ (two-tailed).

Results

Detailed socio-demographic, anthropometric and self-administrated questionnaire results can be found in table III.1, III.2 and III.3, respectively. Most participants considered that Trears use was very comfortable, effective and safe. They also described that its use was more effective, safer and as pleasurable as the use of cotton swabs. Although only 14.3% would be willing to buy this product, most of them said that they might consider that option (60.7%) (Table V.1).

While the amount of the extracted left and right baseline earwax samples did not differ between them, Trears extracted significantly more earwax than the use of the Alexander-Reiner syringe ($p<0.001$) (Table IV.2). Both ears increased significantly their earwax production after the baseline Alexander-Reiner syringe cleaning (both $p<0.05$). The amount of extracted left follow-up earwax sample was also significantly larger than the baseline right earwax sample ($p<0.05$).

Whereas different tip dowels thickness did not show any difference regarding the amount of extracted earwax, those sponges with 50% of humidity or 105.1 µl $MgCl_2$ (Table IV.3) extracted more earwax than those with 12.5% ($p<0.05$) (Table IV.4). No biological or psychological variable varied the amount of secreted earwax (all $p>0.05$) (Table IV.5). While Trears' variants did not change participants' appraisals about their experience using Trears, subjects under an increased number, or more severe hassles considered that its effectivity was poorer and worse than cotton swabs (Table IV.6).

TABLE IV.1

| | | | Trears satisfaction survey | | | |
|---|---|---|---|---|---|---|
| | Questions | | | Results: | | |
| | | | | | Mean | |
| N | | Meaning: | Q1 | Median | (s.d) | Q3 |
| 1 | How would describe your experience using Trears? | 1 = very uncomfortable, 5 = very comfortable | 4 | 4 | 4.0 (1.0) | 5 |
| 2 | How would you describe Trears effectivity for cleaning your outer ears? | 1 = very ineffective, 5 = very effective | 4 | 4 | 4.2 (0.9) | 5 |
| 3 | How safe do you consider that is was the use of Trears inside your ear? | 1 = very unsafe, 5 = very safe | 4 | 4 | 4.3 (0.6) | 5 |
| 4 | Do you know cotton swabs? | n (%) | | Yes 28, (100) | No 0, (0) | |
| 5 | How often do you use cotton swabs? | n (%) | Every day 2, (7.1) | Almost every day 8, (28.6) | Sometimes 8, (28.6) | Seldom 1, (3.6) | Nearly never 3, (10.7) | Never 6, (21.4) |
| 6 | Do you think that the use of Trears was more comfortable than cotton swab? | 1 = extremely disagree, 5 = extremely agree | 2 | 3 | 3.1, (1.4) | 4.5 |
| 7 | Do you think that the use of Trears for cleaning your ears was more effective than cotton swabs? | 1 = extremely disagree 5 = extremely agree | 3 | 4 | 3.9, (1.2) | 5 |
| 8 | Do you think that the use of Trears was safer than cotton swabs | 1 = extremely disagree 5 = extremely agree | 4 | 4 | 4.2, (0.9) | 5 |
| 9 | How would define the design of Trears? | 1 = very unattractive, 5 = very attractive | 3 | 4 | 3.7, (1.0) | 4 |
| 10 | What do you think about the size of Trears? | 1 = too small, 5 = too big | 3 | 3.5 | 3.5, (0.8) | 4 |

TABLE IV.1-continued

Trears satisfaction survey

| N | Questions | Meaning: | Results: Q1 | Median | Mean (s.d) | Q3 |
|---|---|---|---|---|---|---|
| 11 | Would you be willing to buy Trears? | n (%) | No 7, (25.0) | Perhaps 17, (60.7) | Yes 4, (14.3) | |
| 12 | How much would you be willing to pay for one unit of Trears? | Currency (CLP) | Q1 1000 | Median 2000 | Mean (s.d) 3452.5 | Q3 3000 |

TABLE IV.2

Earwax extraction comparisons between the use of the Reiner-Alexander syringe and Trears device.

| Ear | Left | | | | Right | | | | |
|---|---|---|---|---|---|---|---|---|---|
| | Method | | | | | | | | |
| | Reiner-Alexander syringe (mg) | | | | Reiner-Alexander syringe (mg) | | | | |
| Assessment | Q1 | Median | Mean (s.d) | Q3 | Q1 | Median | Mean (s.d) | Q3 | P-value[ω] |
| Baseline (day = 0) | 6.2 | 8.5 | 10.7, (1.1) | 15.7 | 5.1 | 7.9 | 9.2, (0.7) | 13.7 | 0.07 |
| | Method | | | | | | | | |
| | Reiner-Alexander syringe (mg) | | | | Trears (mg) | | | | |
| Assessment | Q1 | Median | Mean (s.d) | Q3 | Q1 | Median | Mean (s.d) | Q3 | P-value[Ψ] |
| Follow-up (day = 30) | 12.0 | 17.3 | 19.1 (1.8) | 19.6 | 79.8 | 124.7 | 155.8 (18.2) | 200.3 | <0.001* |

[ω]p-value was obtained using repeated t-test
[Ψ]p-value was obtained Wilcoxon matched-pairs signed-ranks test
*p-value was significant at 0.05 level.

TABLE IV.3

Trears humidity

| | Volume of $MgCl_2$ | |
|---|---|---|
| % | Mean (μl) | SD (μl) |
| 12.5 | 30 | 0 |
| 25 | 56.6 | 5.2 |
| 30 | 63.7 | 2.5 |
| 50 | 105.1 | 5.6 |

TABLE IV.4

Linear Regression model analyses between Trears' variants and the among of extracted earwax using Trears

| | | Among of extracted earwax by Trears | | |
|---|---|---|---|---|
| Trears Variants | | β | CI | P value |
| Humidity of Trears sponge (%) | 25 | 39.6 | −105.9; 185.2 | 0.58 |
| | 30 | 26.7 | −63.7; 117.2 | 0.55 |
| | 50 | 147.1 | 71.1; 223.2 | <0.01* |
| Thickness of Trears tip (mm) | 4.5 | 19.4 | −67.6; 106.5 | 0.65 |

*p significant at p < 0.05

TABLE IV.5

Linear regression model between analyses between the among of extracted earwax using Trears and some biological and psychological variables

| Variables | β | p-value | CI |
|---|---|---|---|
| Age | 0.6 | 0.78 | −3.8; 5.0 |
| Sex | 53.8 | 0.14 | −19.0; 126.7 |
| Alcohol (unit) [φ] | −2.3 | 0.73 | −16.0; 11.4 |
| Tobacco | −26.0 | 0.54 | −112.9; 60.8 |
| BMI | 4.3 | 0.37 | −5.41, 14.0 |
| Waist circumference | 0.8 | 0.53 | −1.8; 3.4 |
| Anti-conceptive pill | 31.8 | 0.18 | −16.5; 80.2 |
| PSS | −1.0 | 0.72 | −6.9; 4.9 |
| Number of Hassles | −0.2 | 0.91 | −3.8; 3.4 |
| Severity of Hassles | −0.6 | 0.58 | −2.7; 1.6 |
| RLCQ | −0.1 | 0.51 | −3.4; 0.2 |
| Severe RLCQ[Ψ] | −17.6 | 0.43 | −62.7; 27.6 |

[φ]One alcohol unit is measured as 10 ml or 8 g of pure alcohol. This equals one 25 ml single measure of whisky (Alcohol by volume [ABV] 40%), or a third of a pint of beer (ABV 5-6%) or half a standard (175 ml) glass of red wine (ABV 12%).
[Ψ]Recent Life Event Questionnaire

TABLE IV.6

Linear regression models between some Trears satisfaction survey question results and some psychological variables or Trears' variants

| | | Trear's satisfaction survey questions | | | | | | | | | | | |
|---|---|---|---|---|---|---|---|---|---|---|---|---|---|
| | | How would you describe Trear's effectivity? | | | How would you describe your user experience? | | | Do you think that Trears was more effective than cotton swabs for cleaning your ears? | | | Do you think that the use of Trears was more comfortable than cotton swabs? | | |
| | | $R_s$ | p-value | CI | $R_s$ | p-value | CI | $R_s$ | p-value | CI | $R_s$ | p-value | CI |
| Trears Variables | | | | | | | | | | | | | |
| Among of extracted earwax by Trears (mg) | | 5.7 | 0.80 | 41.5; 53 | 13.5 | 0.59 | <−64.7; 37.8 | −4.7 | 0.80 | −43.8; 34.3 | 16.7 | 0.29 | −15.3; 46.7 |
| Humidity | 25 | 0.3 | 0.72 | 1.4; 2.0 | 0.4 | 0.6 | −1.2; 1.9 | −0.1 | 0.9 | −2.1; 1.9 | −0.2 | 0.87 | −2.8; 2.4 |
| Humidity | 30 | −0.7 | 0.19 | −1.9; 0.4 | −0.7 | 0.17 | −1.8; 0.4 | −1.5 | 0.04* | 2.9; −0.1 | −0.3 | 0.70 | −2.1 1.4 |
| Humidity | 50 | <0.1 | 0.97 | −1.0; 1.1 | −0.5 | 0.34 | −1.4; 0.5 | 0.7 | 0.23 | −1.9; 0.5 | −0.1 | 0.89 | −1.5; 1.7 |
| Dowel thickness | | 1.5 | 0.80 | 0.21; 3.17 | −0.1 | 0.88 | −1.1; 0.9 | −0.2 | 0.65 | 0.89; 0.56 | 0.12 | 0.70 | −0.52; 0.77 |
| Psychological Variables | | | | | | | | | | | | | |
| Environ. factor: | No. of hassles | −0.4 | 0.90 | −4.7; 3.9 | −5.2 | 0.02* | −9.4; 0.9 | −3.9 | 0.02* | −7.2; 0.7 | −0.9 | 0.51 | −3.9; 2.0 |
| Environ. Factor: | Severity of hassle | 1.0 | 0.75 | −8.2; 6.2 | −7.9 | 0.03* | −15.1; 0.8 | −5.6 | 0.04* | −11.1; 0.1 | −1.4 | 0.58 | −6.4; 3.5 |
| Environ. Factor | No. of life events | −19.2 | 0.48 | −74.6; 36.2 | −18.5 | 0.53 | −79.1; 42.0 | −29.4 | 0.18 | −74.2; 15.3 | −7.5 | 0.69 | −46.4; 31.4 |
| Environ. Factor | Severity of life events | <0.01 | 0.83 | −0.5; 0.4 | −0.3 | 0.10 | 0.7; 0.1 | −0.6 | 0.03* | 1.1; −.04 | 0.2 | 0.57 | 0.9 0.5 |
| Environ. Factor | Perceived stress | 1.8 | 0.16 | −0.8; 4.3 | 0.9 | 0.50 | −1.9; 3.8 | 1.4 | 0.17 | −0.7; 3.5 | 1.3 | 0.12 | −0.4; 3.0 |
| Trears satisfaction survey question | How often do you use cotton swabs | 0.4 | 0.23 | −0.3; 1.1 | −0.2 | 0.55 | −1.0; 0.5 | −0.1 | 0.85 | −0.6; 0.5 | −0.3 | 0.23 | −0.7; 0.2 |

Discussion

It was found that earwax production increased significantly after the baseline cleaning with the use of the Alexander-Reiner syringe in both ears. Trears removed more earwax than the clinical method (the Alexander-Reiner syringe). Most participants considered that the use of Trears was comfortable, effective and safe. They also reported that its use was more effective, safer and as comfortable than the use of cotton swabs. Although only 14.3% would be willing to buy this product, most participants said that they might consider that option (60.7%).

It is noticeable that, irrespective of the extraction method used, the amount of earwax, rather than decreasing, significantly increased during the follow-up period. It may be explained because, after the baseline cleaning, the ceruminous glands increased their earwax production, acting as a compensatory mechanism, due to the lack of earwax, caused by the baseline outer ear cleaning that was done with the Alexander-Reiner syringe. That difference may also be understood by the characteristic of our study protocol. We instructed participants to avoid cleaning their ears during the follow-period in order to extract a standardised amount of earwax that represents the retrospective month of earwax production. This possibility is also reinforced after observing that 35.7% of the participants were heavy cotton swab users, and another 28.6% make, at least a sporadic use of them.

The use of the Alexander-Reiner syringe, in addition to warm water extracted slightly more earwax (2.25±0.18 mg/week) than the most effective extracted method used by Cipriani et al. (1986) which combined the effect of one unspecified mechanic method of extraction that injected one solution of alcohol/ether 3:1 v/v (2.02±0.22 mg/week). There were confirmed previous Cipriani et al. (1986)'s results, after comparing the baseline results that no earwax volume variation was related to the ear side. However, the baseline volume of earwax did not represent the secreted amount of earwax one month after, since Trears extracted more than eight times more earwax than the syringe in healthy mixed race people.

Although highly inadvisable, the use of cotton swabs will continue to rise. Therefore, designing a safe alternative is a current need. Unfortunately, all current self-cleaning products or devices show none or minimum effect in comparison to the clinical use of the Alexander-Reiner syringe. However, Trears showed that not only is as useful as the traditional method for removing earwax, but it was also capable of extracting even more earwax than that clinical method. Conversely, Trears' tips material was made with one specific abrasive and absorptive cellular sponge that previously showed its utility for removing artificial liquid wax. Furthermore, Trears tip has also incorporated one mineral oil that has already shown some effect on removing earwax. It was confirmed that a larger concentration (50%) of one type of mineral oil, such as magnesium chloride also increased Trears extraction in comparison to those devices that used dryer tips (12.5%). Future Trears device will contain that level of humidity. Then, the additive effect, given by the tip material plus the mineral oil may explain the significant results.

Measuring the Average Glucose Concentration Using Earwax

Background: An increase in the average of glucose concentration is associated with epidemic and chronic illnesses. Currently, no single test is only accurate, but also affordable, convenient and innocuous for reflecting that long-term level. Earwax may meet those characteristics. The applicant associated fasting and postprandial levels of glycaemic with baseline and follow-up samples of earwax and glycated haemoglobin ($HbA_{1c}$).

Methods: 37 healthy participants provided two right earwax and two serum samples that were taken one month apart. The baseline measures were taken after 8 hours of fasting and the follow-up samples were taken after the intake of one standardised meal. While the baseline Earwax Glucose Concentration (EGC) represented the average concentration of previous reprospective fasting and postprandial glucose levels, the follow-up EGC represented the same average over the last month. Both $HbA_{1c}$ samples represented the retrospective average glucose concentration of a period between one and three months. The glycaemic mean was calculated using the average between its respective baseline and follow-up measure. Baseline and follow-up levels of each specimen were compared between them. The effect of several covariates was investigated in these specimens. Fasting Serum Glucose [FSG] was correlated with its respective baseline EGC and $HbA_{1c}$ sample. The same correlation was done between Postprandial Serum Glucose [PSG] and their respective follow-up EGC and $HbA_{1c}$ sample. The mean glycaemic level was correlated with all aforementioned $HbA_{1c}$ and EGC samples. Different glycaemic levels were predicted using baseline and follow-up EGC and $HbA_{1c}$ samples.

Results: All follow-up concentrations were larger than their respective baseline concentration. Earwax samples were not affected by any covariate. While all associations between EGC and glycaemic levels showed high positive correlations (all R>0.60; p<0.001), $HbA_{1c}$ associations with different glycaemic levels exhibited either moderate or low correlations (all R<0.50; 0.10<p<0.01). The baseline EGC predicted the largest increased in the mean of glycaemic levels (all p<0.001).

Conclusion: EGC is more accurate than HbA1c for reflecting glycaemic levels. Earwax is more stable than blood sugar and HbA1c for measuring glucose concentration. EGC results suggested that earwax better represents the mean glucose level over long-term.

Although glucose levels have already been measured in earwax samples elsewhere (Masuda et al, 1978; Shichjo & Masuda, 1979; Herane-Vives & Benohr, 2018), even in diabetic patients (Khasanov & Popova, 1984), it is unknown whether the found EGC in those previous studies accurate represent the glycaemic levels. That is why in this study we measured EGC, glycaemic and $HbA_{1c}$ levels that were taken during fasting and after one standardised meal in a sample of healthy participants. Baseline and follow-up levels of each specimen were compared between them. The effect of several covariates on their glucose levels was also investigated. Fasting Serum Glucose [FSG] was correlated with its respective baseline EGC and $HbA_{1c}$, and the same correlation was done between Postprandial Serum Glucose [PSG] and its respective follow-up EGC and $HbA_{1c}$ levels. The mean glucose level was correlated with all the aforementioned $HbA_{1c}$ and EGC samples. Different glycaemic levels were predicted using baseline and follow-up EGC and $HbA_{1c}$ samples.

It was hypothesized that: 1) All follow-up concentrations would be larger than their respective baseline concentration; 2) Earwax would be a more stable than glycaemic and $HbA_{1c}$ levels for reflecting the glucose concentration; 3) All associations between EGC and different glycaemic levels would be stronger than the associations between $HbA_{1c}$ and the same glycaemic measures; and 4) the baseline EGC would predict the largest increase in the mean of glycaemic levels.

Methods 37 healthy participants provided two right earwax and two serum samples that were taken one month apart. The baseline measures were taken after 8 hours of fasting and the follow-up samples were taken after the intake of one standardised meal. While the retrospective time period of earwax glucose accumulation is unknown, the follow-up EGC covered the last month of accumulation. Both $HbA_{1c}$ samples represented the retrospective average glucose concentration of a period between one and three months. The mean of glycaemic level was calculated using the average between its baseline and follow-up glycaemic levels. Baseline and follow-up levels of each specimen were compared between them. The effect of several covariates was investigated in these specimens. Fasting Serum Glucose [FSG] was correlated with its respective baseline EGC and $HbA_{1c}$, and the same was done between Postprandial Serum Glucose [PSG] and their respective follow-up EGC and $HbA_{1c}$. The mean of glycaemic level was correlated with all aforementioned $HbA_{1c}$ and EGC measures.

Earwax Samples

Right baseline earwax sample was collected after 8 hours of fasting. Right follow-up earwax sample was collected two hours after the commencement of intake a standardised liquid meal of 236 ml of Ensure Avance®. All samples were labelled and store at 4 degree Celsius.

Earwax Samples Using the Alexander-Reiner Siringe

Earwax samples obtained by ear wash were processed by drying them using the $N_2$ displacement method. Briefly, each of the 50 ml was separated into 4 tubes, each of which was inserted a cannula connected to a $N_2$ gas tank, maintaining a constant temperature of 25° C. using a thermoregulated bath. When the $N_2$ flow is opened, it displaces the $H_2O$ which evaporates, thus allowing the sample to dry. Once the basal samples were dried as the left sample obtained at day 30, the weight of the dry cerumen sample was obtained by subtracting the weight of the tubes with dry sample less the weight of the empty tube (previously weighed). Finally, 125 μl of PBS was added to each tube, the contents of each tube were resuspended, and the samples were combined in a single 5 ml tube, which contained the total of the sample resuspended in 500 μl of PBS and stored at 4° C. until use.

Earwax Samples Using Trears

The earwax samples obtained by using the TEARS® instrument were processed by washing the sponge with 500

µl of PBS for 2 minutes. However, the drying time with $N_2$ was much less since the extraction mechanism of Trears is dry. Indeed, conversely to Alexander-Reiner syringe Trears does not inject water.

In detail, 500 µl of a buffer solution, PBS were added to a 5 ml tube, the sponge was separated from its plastic support and introduced into the tube. After the sponge absorbed the entire solution, the sponge was repeatedly squeezed and absorbed for a period of 2 minutes, and then the sponge was squeezed dry and removed from the tube. Subsequently, the resulting solution was dried by displacement with N2 and the content was resuspended in 500 µl of ultrapure water. The resulting solution in the tube was stored at 4° C. until use.

Serum Samples

The fasting blood samples were taken (with a 3 cc syringe in the antecubital vein and using a blood collection tube without anticoagulant). All serum samples were taking during morning. One $HbA_{1c}$ and glycaemic sample [FSG] were taking during the morning of the baseline visit. Participants were previously instructed to avoid eating or drinking anything eight hours before that assessment. Another $HbA_{1c}$ and glycaemic sample [PSG] were taken during the follow-up visit. Those follow-up samples were taken two hours after the commencement of intake a standardised liquid meal of 236 ml of Ensure Avance® which contains 1.5 kcal/ml, given by 24.3% protein, 44.8% carbohydrate 28.8% fat, 1% fibre and 1.1% Beta-hydroxy-beta-methyl butyrate. The mean glucose concentration in serum was estimated from the average between fasting and postprandial glycaemic levels.

Serum Glucose Analysis

Preparation of serum samples. The blood samples obtained in fasting and postprandial conditions were stored at 4° C. for 24 hours, in order to allow the coagulation and separation of the serum and then centrifuged at 1000×g for 20 minutes at 4° C. Subsequently the serum was separated from the pellet using a 1 ml syringe and collecting them in 2 ml plastic tubes properly labeled. Once the serums were obtained, they were stored at −20° C. until their use.

Quantification of Glucose from Samples of Cerumen and Serum

The amount of glucose was quantified by the use of enzymatic oxidation assays and oxidized glucose labeling in 96-well plates, according to the instructions given by their suppliers (BioVision Inc., Milpitas, CA, USA), using a standard curve of 0, 2, 4, 6, 8 and 10 nmol of Glucose standard per well. 50 µl of standards, aqueous fraction and a 1:25 dilution of serums were added to the remaining wells together with 50 µl of Glucose ration Mix, containing glucose assay Buffer, 2 µl of glucose probe and 2 µl of enzymatic glucose mix. The mixture was incubated for 30 min at 37° C., protected from light, for immediately after measuring the absorbance at 570 nm in a microplate reader (NovoStar). The absorbance of the standard curve was adjusted to an equation of the line and the glucose content was calculated by interpolation within the adjusted curve.

Quantification of Glycosylated Hemoglobin from Serum Samples

The amount of glycosylated hemoglobin (HbA1c) was quantified by the use of sandwich ELISA, according to the instructions given by its suppliers (Abbexa Ltd., Cambridge, UK), using a standard curve of 0.30125, 6.25, 12.5, 25, 50, 100 and 200 ng/ml of HbA1c standard. standards and 100 µl standards and undiluted serums were added to the wells of a plate coated with an antibody against HbA1c, which were incubated for 90 minutes at 37° C. with shaking. After discarding the contents and washing 2 times with washing solution, 100 µl of a HbA1c detection antibody conjugated with Biotin was added, and then incubated for 60 minutes at 37° C. with shaking. After discarding the contents and washing 3 times with wash buffer, they added 100 µl of a solution of Estrepatavidin conjugated with Rabinito Peroxidase (HRP) to each well and incubated for 30 min at 37° C. with shaking. After discarding the contents and washing 5 times with wash buffer, 90 µl of TMB substrate was added to each well and incubated in the dark at 37° C. for 20 minutes. Finally, 50 µl of reaction stop solution was added to each well and the absorbance at 450 nm was quantified in a microplate reader (NovoStar). The absorbance of the standard curve fits a straight line and the absorbances of the samples are interpolated in said curve.

Statistical Analysis

The data were checked for normality using the Kolmogorov-Smirnov statistical test and graphics methods. All other values were normally distributed (all $p>0.05$). Therefore, there were used repeated t-tests for comparing baseline and follow-up glucose levels using the different specimens. Linear regression analysis was used to determine the association between glucose concentration and different biological and psychological variables and to predict different glycaemic levels using EGC and $HbA_{1c}$ specimens. Pearson correlations was used to determine associations between baseline and follow-up EGC and different glycaemic levels or between baseline and follow-up $HbA_{1c}$ and different glycaemic levels. Cohen's criteria for correlations were used: low when $r=0.1-0.3$, moderate when $r=0.3-0.5$ and high when $r=0.5-1.0$ (J Cohen, 2013). The time needed for analysing each specimen was also recorded. The level of significance was set at $p≤0.05$ (two-tailed).

Results

Figure 5:
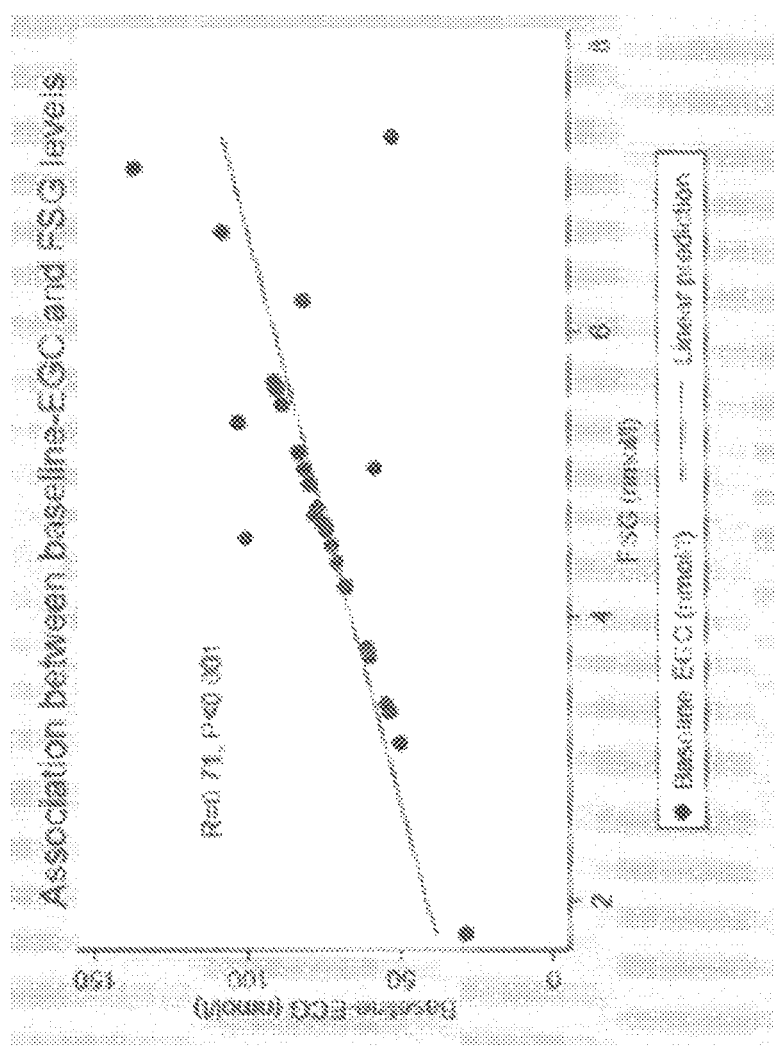
FIG. 5 is a graph showing the results of the association between Baseline-EGC and FSG.
Figure 6:
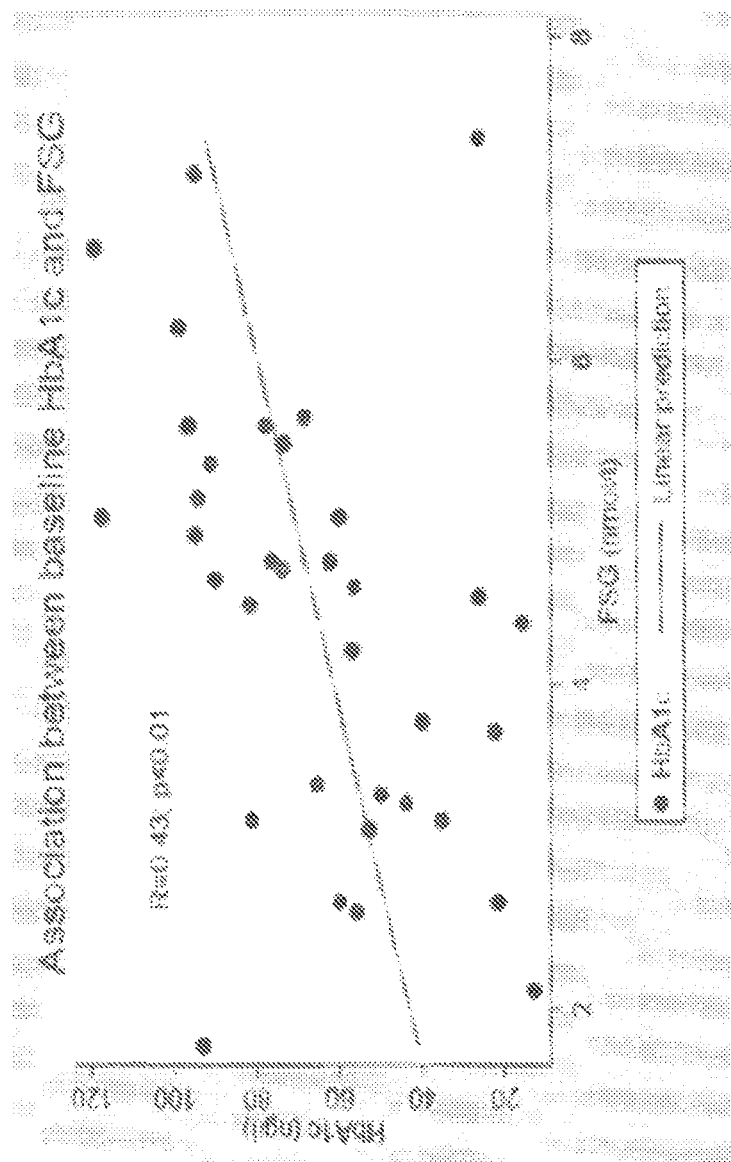
FIG. 6 is a graph showing the results of the association between Baseline-HbA1c and FSG.
Figure 7:
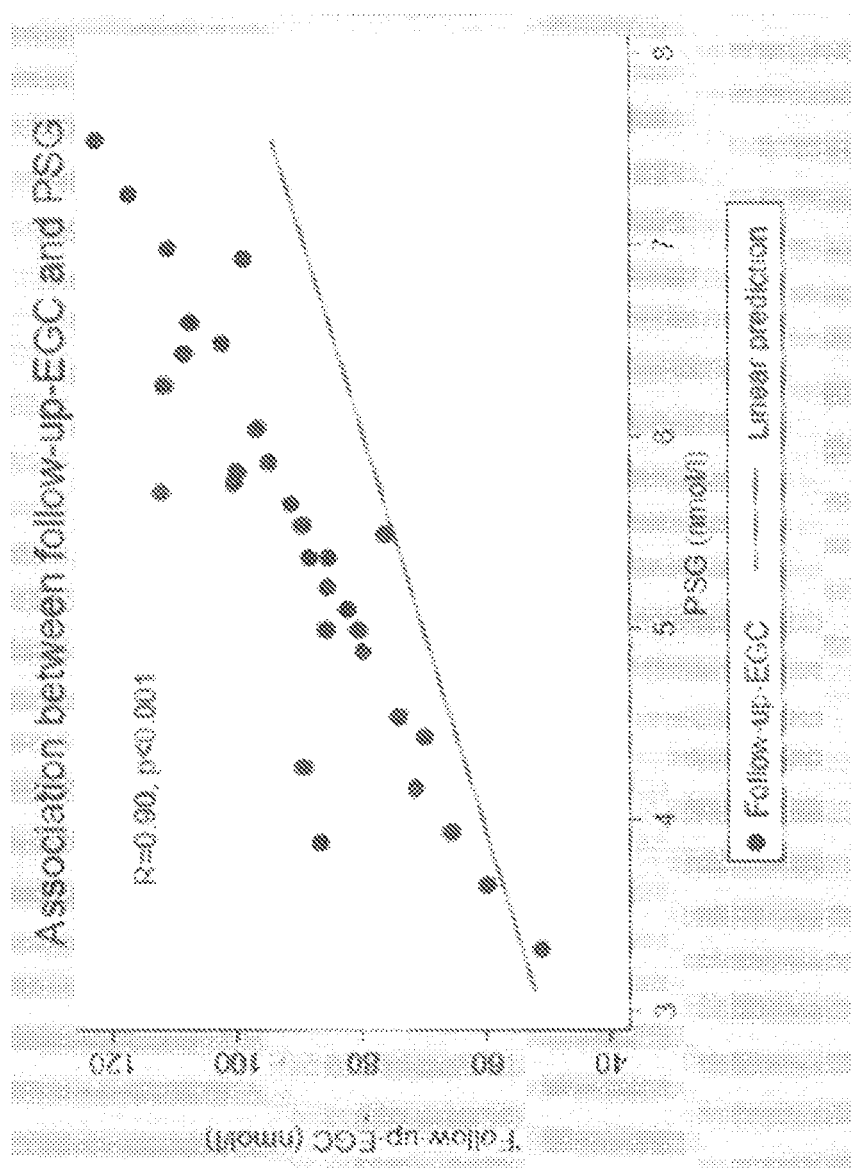
FIG. 7 is a graph showing the results of the association between follow-up-EGC and PSG.
Figure 8:
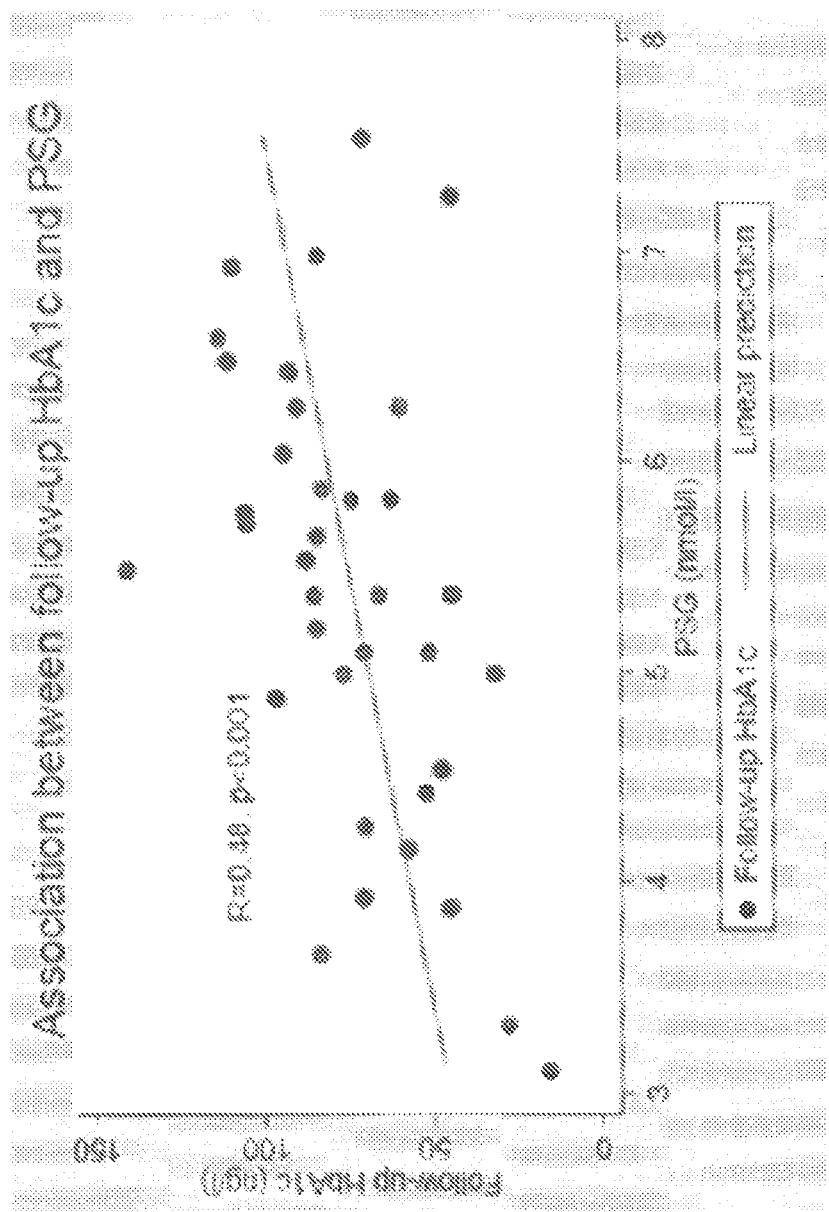
FIG. 8 is a graph showing the results of the association between follow-up-HbA1c and PSG.
Figure 9:
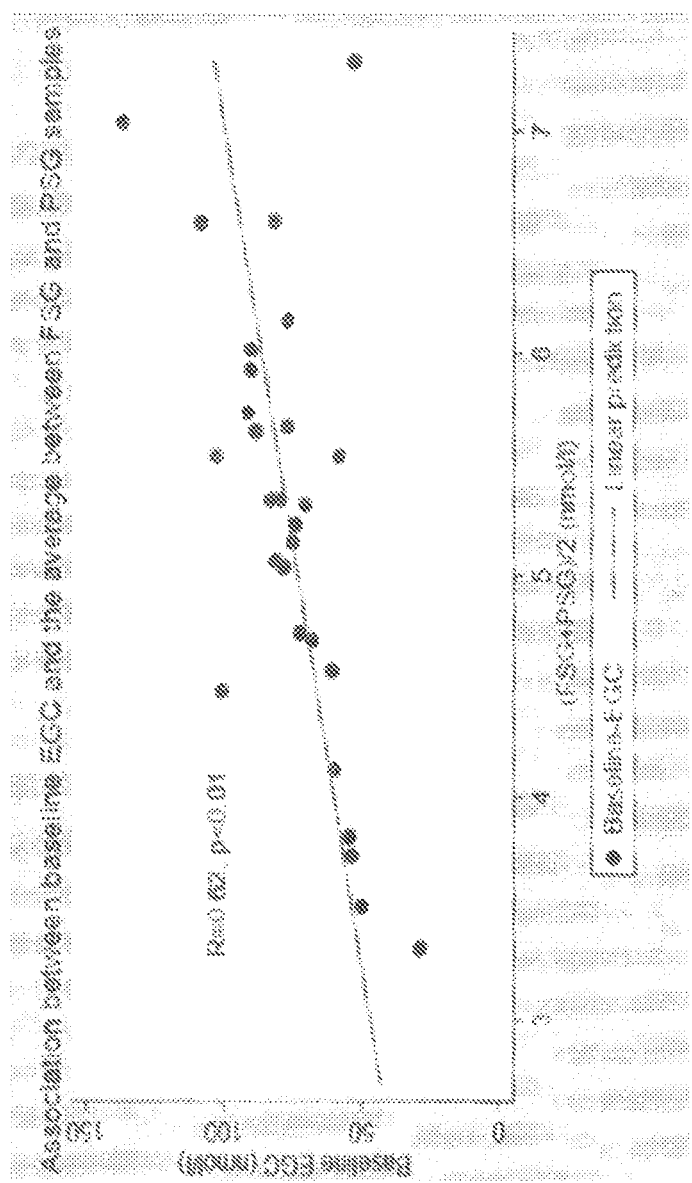
FIG. 9 is a graph showing the results of the association between baseline. EGC and the mean of glycaemic levels.
Figure 10:
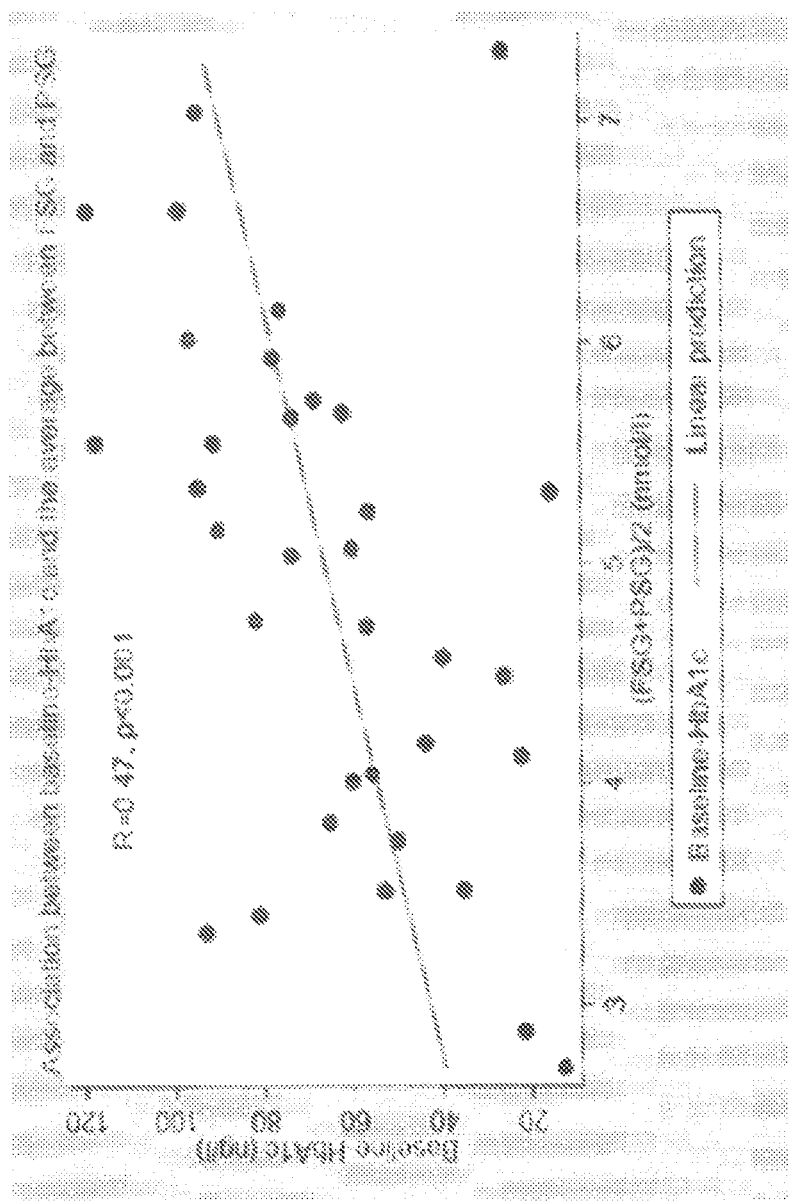
FIG. 10 is a graph showing the results of the association between Baseline-HbA1c and the mean of glycaemic levels.
Figure 11:
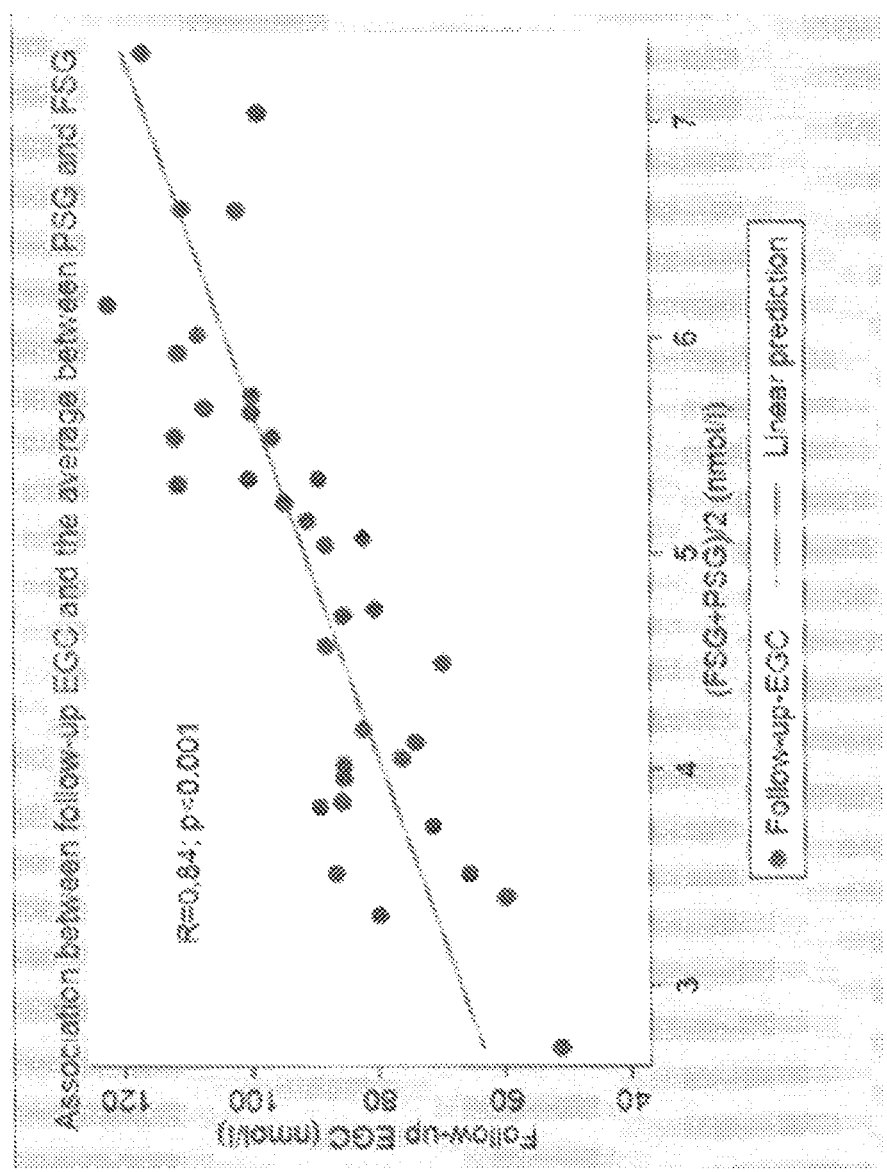
FIG. 11 is a graph showing the results of the association between Follow-up-EGC and the mean of glycaemic levels.
Figure 12:
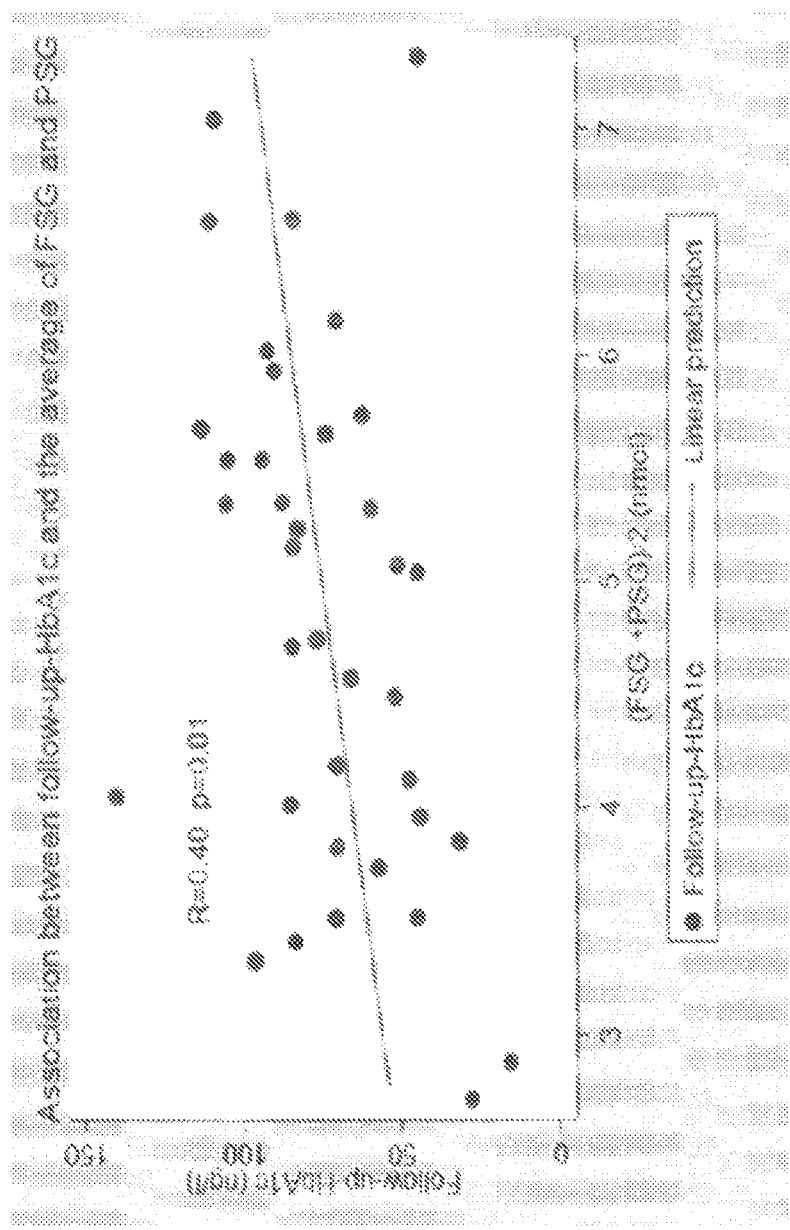
FIG. 12 is a graph showing the results of the association between Follow-up-HbA1c and the mean of glycaemic levels.

Detailed socio-demographic, anthropometric and self-administrated questionnaire results can be found in table III.1, III.2 and III.3, respectively. The use of Trears significantly decreased the time needed for analysing earwax, in comparison to the time needed when the Alexander-Reiner syringe was used (compare tables II.4 and V.1). All follow-up concentrations were larger than their respective baseline concentration (Table V.2). Earwax samples were more stable than $HbA_{1c}$ or glycaemic levels, since their glucose concentration were not affected by any covariate (Table V.3). Age has a direct effect on baseline $HbA_{1c}$ sample. Furthermore, while an increased number of years of education increased follow-up the $HbA_{1c}$ and PSG levels, smoking decreased FSG and PSG levels (Table V.3). Whereas all associations between EGC and glycaemic levels showed high positive correlations (all $R>0.60$; $p<0.001$), $HbA_{1c}$ associations with different glycaemic levels exhibited either moderate or low correlations (all $R<0.50$; $0.10<p<0.01$) (FIGS. 5, 6, 7 and 8). The follow-up $HbA_{1c}$ showed a stronger correlation with FSG ($R=0.48$, $p<0.001$) than the association between the baseline $HbA_{1c}$ and FSG ($R=0.43$, $p<0.001$) (FIGS. 6 and 8). Both EGC associations were stronger than HbA1c association. However, the follow-up EGC sample also showed a stronger association with PSG (R=0.90, p<0.001) (FIG. 7), than the baseline-EGC sample with FSG levels (R=71 p<0.001) (FIG. 5). The mean glycaemic level also showed a stronger association with earwax, rather than HbA1c specimens (see both FIGS. 9, 10 and 11, 12) and, among them, the postprandial earwax sample showed also the strongest association with the mean glycaemic level (R=0.84, p<0.001) (FIG. 11).

TABLE V.1

Time needed to analysing different specimens
tiempo de cuantificación

| PROCESS | Cortisol in washing of ears | cortisol using TEARS | Glucose in washing of ears | Glucose using TEARS | Cortisol in serum | HbA 1c in serum | Serum glucose |
|---|---|---|---|---|---|---|---|
| Centrifugation of the sample | 00:00:00 | 00:00:00 | 00:00:00 | 00:00:00 | 00:20:00 | 00:20:00 | 00:20:00 |
| Drying of the sample with N2 prior to extraction | 08:30:00 | 00:47:00 | 08:30:00 | 00:47:00 | 00:00:00 | 00:00:00 | 00:00:00 |
| Extraction of the sample with organic solvent | 02:10:00 | 02:10:00 | 02:10:00 | 02:10:00 | 00:00:00 | 00:00:00 | 00:00:00 |
| Drying of the sample after extraction | 00:40:00 | 00:40:00 | 00:40:00 | 00:40:00 | 00:00:00 | 00:00:00 | 00:00:00 |
| Quantification protocol | 04:00:00 | 04:00:00 | 01:00:00 | 01:00:00 | 04:00:00 | 04:00:00 | 01:00:00 |
| TOTAL TIME | 15:20:00 | 07:37:00 | 12:20:00 | 04:37:00 | 04:20:00 | 04:20:00 | 01:20:00 |

TABLE V.2

Baseline and follow-up time. Glucose. HbA 1c and EGC level comparisons

| Ear | Right | | | | Right | | | | p-value |
|---|---|---|---|---|---|---|---|---|---|
| | Time in the morning h +/− SD | | | | | | | | <0.05 |
| | 8:41 +/− 00:50 | | | | 10:53 +/− 00:44 | | | | |
| | Sample | | | | | | | | |
| | Baseline-EGC (nmol/l) | | | | Follow-up-EGC (nmol/l) | | | | |
| | Q1 | Median | Mean (s.d.) | Q3 | Q1 | Median | Mean (s.d.) | Q3 | P-Value |
| Results | 60.5 | 76.9 | 76.7 (4.0) | 82.5 | 81.5 | 88.9 | 94.7 (2.9) | 101.5 | <0.01 |
| | Sample | | | | | | | | |
| | Baseline-HbA:c (ng/l) | | | | Follow-up HbA:c (ng/l) | | | | |
| | Q1 | Median | Mean (s.d.) | Q3 | Q1 | Median | Mean (s.d.) | Q3 | P-Value |
| Results | 43.9 | 65.4 | 65.4 (4.0) | 91.2 | 52.1 | 74.0 | 75.8 (4.1) | 90.2 | <0.01 |
| | Sample | | | | | | | | |
| | FSG (nmol/l) | | | | PSG (nmol/l) | | | | |
| | Q1 | Median | Mean (s.d.) | Q3 | Q1 | Median | Mean (s.d.) | Q3 | P-value |
| Results | 3.2 | 4.5 | 4.3 (0.3) | 5.2 | 4.9 | 5.4 | 5.4 (0.2) | 6.0 | <0.01 |

[0]p-value was obtained using repeated t-test.
*p-value was significant at 0.05 level.
HbA:c: Glycated haemoglobin.
FSG: Fasting Serum Glucose.
PSG: Postprandial Serum Glucose.

TABLE V.3

Linear regression models between several covariates and baseline and follow-up earwax, glycaemic and HbA1c samples.

| Variables | Baseline-EGC (nmol/l) | | | Follow-up-EGC (nmol/l) | | | Baseline-HbA:c (ng/l) | | |
|---|---|---|---|---|---|---|---|---|---|
| | β | P-value | Cl | β | P-value | Cl | β | P-value | Cl |
| Age | 0.4 | 0.38 | −0.6; .1.4 | 0.3 | 0.29 | −0.3 | 1.1 | 0.05 | <0.1; 2.2 |
| Sex | −5.2 | 0.50 | −22.3; 11.3 | 2.9 | .0.70 | −9.3; 13.5 | −11.1 | 0.26 | −30.5; 8.6 |
| Secondary school or technical | 3.1 | 0.54 | −11.9; 22.1 | 9.1 | 0.10 | −1.9; 20.0 | 0.6 | 0.44 | −124; 27.0 |
| Alcohol | 40 | 0.18 | −1.9; 10.0 | −1.3 | 0.19 | −34; 0.7 | 1.3 | 0.47 | −2.3; 4.8 |
| Tobacco | −9.9 | 0.40 | −33.7; 13.9 | −10.5 | 0.13 | −23.2; 3.1 | −13.1 | 0.36 | −35.5; 10.4 |
| BMI | −1.3 | 0.17 | −33; 0.6 | −0.9 | 0.18 | −2.4; 0.5 | −1.3 | 0.29 | −3.9; 1.2 |
| Waist circumference | 0.24 | .036 | −0.8; 0.3 | −0.1 | 0.72 | −0.5; 0.3 | −0.4 | 0.24 | −1.1; 0.3 |
| Anti-contraceptive pill | 10.2 | 0.17 | −5.0; 25.4 | 4.2 | 0.53 | −9.7; 18.0 | −7.5 | 0.84 | −39.2; 24.3 |
| PSS | −0.8 | 0.21 | −2.1; 3.5 | −0.1 | 0.94 | −0.9; 0.8 | −0.2 | 0.87 | −1.7: 1.4 |
| Number of Hassles | −0.1 | 0.94 | −09; 0.9 | −0.3 | 0.23 | −0.8; 0.2 | 0.4 | 0.39 | −0.5; 1.4 |
| Severity of Hassles | <0.1 | 0.98 | −0.5; 0.5 | −0.1 | 0.45 | −0.4; 0.2 | 0.3 | 0.30 | −0.3; 0.9 |
| RLCQ | <0.1 | 0.54 | <0.1; <0.1 | <0.1 | 0.79 | <−0.1; <0.1 | <−0.1 | 0.70 | <0.1; <0.1 |
| Severe RLCQ | 3.0 | 0.54 | −13.3; 7.2 | <−0.1 | 0.99 | −0.7; 7.0 | 1.6 | 0.79 | −10.6; 13.8 |

| Variables | Follow-up HbA:c (ng/l) | | | FSG (nmol/l) | | | PSG (nmol/l) | | |
|---|---|---|---|---|---|---|---|---|---|
| | β | P-value | Cl | β | P-value | Cl | β | P-value | Cl |
| Age | 1.7 | <0.0; 0.1 | 0.8 2.6 | <0.01 | 0.27 | <−0.1; <0.1 | <0.1 | 0.07 | <−0.1; <0.1 |
| Sex | −2.7 | 0.30 | −20.5; 18.0 | −0.1 | 0.84 | −1.0; 0.9 | 0.1 | 0.81 | −3.6; 0.8 |
| Secondary school or technical | 18.0 | 0.04* | 0.7; 35.3 | 0.4 | 0.35 | −0.5; 1.4 | 0.7 | 0.04* | <0.1; 1.4 |
| Alcohol | 0.2 | 0.90 | −3.1; 3.5 | −0.1 | 0.51 | −0.2; 0.1 | 0 | 0.18 | 0.2; |
| Tobacco | −194 | 0.05 | −39.5; 0.7 | −1.3 | .001 | −2.3; −0.3 | −0.9 | 0.02* | −1.7; 0.3 |
| BMI | −1.1 | 0.36 | −3.4; 1.3 | <−0.1 | 0.74 | −0.1; 0.1 | <−0.1 | 0.43 | −0.1; 0.1 |
| Waist circumference | −0.4 | 0.24 | −0.9; 0.3 | <0.1 | 0.73 | <0.1; <0.1 | <−0.1 | 0.68 | <−0.1; <0.1 |
| Anti-contraceptive pill | 9.4 | 0.41 | −14.7; 33.5 | 0.74 | 0.13 | −0.2; 1.7 | 0.1 | 0.74 | −0.6; 0.8 |
| PSS | 0.8 | 0.23 | −0.6; 2.3 | <0.1 | 0.88 | −0.1; 0.1 | −0.1 | 0.57 | <−0.1; 0.1 |
| Number of Hassles | 0.4 | 0.38 | −0.5; 1.2 | −1.0 | 0.84 | <0.1; −0.1 | <.01 | 0.86 | <−0.1; −0.1 |
| Severity of Hassles | 0.3 | 0.23 | −0.2; 0.8 | −0.1 | 0.78 | <0.1; <0.1 | <0.1 | 0.86 | <0.1; <0.1 |
| RLCQ | <−0.1 | 0.42 | −0.1; −0.1 | <−0.1 | 0.83 | <−0.1; −0.1 | <0.1 | 0.97 | <−0.1; −0.1 |

TABLE V.3-continued

Linear regression models between several covariates and baseline and follow-up earwax, glycaemic and HbA1c samples.

| | | | | | | | | | |
|---|---|---|---|---|---|---|---|---|---|
| Severe RLCQ | 3.7 | 0.50 | −14.6; 7.3 | −0.1 | 0.86 | −0.6; 0.5 | <−0.1 | 0.86 | .0.5; 0.4 |

PSS: Perceived Stress Scale.
RLCQ: Recent Life Event Questionnaire.
HbA:c: Glycated haemoglobin.
EGC: Earwax Glucose Concentration.
FSG. Fasting Glycaemic Levels.
PSG: Postprandial Serum Glucose ∝ One alcohol unit is measured as 10 ml or 8 g of pure alcohol.
This equals one 25 ml angle measure of whisky (Alcohol by volume (ABV) 40%), or a third of a pint of beer (ABV 5-6%) or half a standard (175 ml) glass of red wine (ABV 12%) for comparison to under or postgraduate studies.

Please see FIGS. 5, 6, 7, 8, 9, 10, 11 and 12

TABLE V.4

Linear regression models between baseline, follow-up and means values of fasting, postprandial and HbA1c samples and FSG, PSG and mean glycaemic levels

| | Glycaemic samples | | | | | | | | |
|---|---|---|---|---|---|---|---|---|---|
| Earwax and | FSG (nmol/l) | | | PSG (nmol/l) | | | The glycaemic mean | | |
| HbA., Samples | β | p-value | CI | β | p-value | CI | β | p-value | CI |
| Baseline EGC (nmol/l) | 12.4 | −0.001* | 7.4; 17.4 | 9.5 | 0.02* | 1.3; 17.8 | 13.2 | <0.001* | 6.5; 18.8 |
| Follow-up EGC (nmol/l) | `8.4 | <0.001* | 5.4; 11.3 | 14.5 | <0.001 | 12.1; 17.0 | 12.4 | <0.001* | 9.6; 15.1 |
| Baseline HbA(ng/l) | 9.2 | <0.01 | 2.5; 15.8 | 11.9 | <0.01 | 3.8; 20.1 | 11.7 | <0.01* | 4.0; 19.4 |
| Follow-up HbA (ng/l) | 5.8 | 0.07 | −0.4; 12.1 | 12.0 | <0.01 | 4.5; 19.5 | 9.5 | 0.01* | 2.2; 16.7 |

EGC: Earwax glucose concentration.
FSG: Fasting serum glucose.
PSG: Postprandial serum glucose.
HbA: Glycaemic fasting glucose.
The means of EGC, glycaemic, and HbA are calculated as the mean between the baseline and follow-up sample.
*P-value significant at 0.05.

Discussion

It was found that all follow-up concentrations, using glycaemic, $HbA_{1c}$ and EGC specimens were significantly larger than their respective baseline concentration, confirming that the study was appropriately conducted. Earwax was a more stable specimen than $HbA_{1c}$ and glycaemic samples, since their glucose levels were not affected by any covariate. While all associations between EGC and glycaemic levels showed high positive correlation coefficients (all R>0.60; p<0.001), $HbA_{1c}$ associations between both glycaemic levels only exhibited moderate or low correlations (all R<0.50; 0.10<p<0.01). Both follow-up EGC and $HbA_{1c}$ measures showed the strongest correlation with the PSG correlation found was between the follow-up EGC and PSG (R=0.90, p<0.001 and R=0.48, p<0.01, respectively). However the largest increase in glycaemic levels were predicted by the baseline EGC and $HbA_{1c}$ (β=13.2, p<0.001; β=11.7, p<0.01, respectively).

There were corroborated previous results that indicate that the strength of the association between $HbA_{1c}$ c using either fasting or postprandial glycaemic levels are very modest in healthy people (van't Riet et al., 2010). This may be explained by the moderate side of the sample, or because $HbA_{1c}$ normally shows an increased association in people who have increased glucose levels, such as those seen in diabetic patients (van't Riet et al., 2010).

It is important to highlight that the time period when the baseline EGC is not completely comparable with its follow-up sample, since they represented different periods of glucose accumulation by earwax. Indeed, the study design only allowed us, prior to the conduction of a baseline outer ear cleaning to standardise the amount of secreted earwax of the follow-up samples. It may be possible that some previous episodes of intense physical activity or some stressful events had momentarily increased the baseline EGC sample. In that sense, the baseline-EGC may represent the long-term accumulation of several episodes of fasting and postprandial glycaemic levels. However, the fact that the largest increase in the mean of glycaemic levels had been predicted not only by the baseline HbA1 measure, but also by the baseline EGC, suggests that EGC better represent the average glucose concentration, rather than its fasting or postprandial concentration. It is well-know that HbA1c is mainly influenced by FSG, rather than PSG, due to the fact that people spend more time fasting than eating during the day (Monnier et al., 2006). Indeed, the baseline EGC may be also mainly influenced by the fasting glucose levels, since that glucose concentration was lower than its follow-up earwax sample (p<0.01).

Earwax is certainly better than $HbA_{1c}$ for reflecting glucose levels. Not only because all correlations between EGC and glycaemic levels were much stronger than the observed correlation coefficients between HbA1c and blood sugar levels, but also because the correlation between the follow-up EGC and PSG showed a stronger association (R=0.90; p<0.001) than the relationship between the baseline EGC and FSG (R=0.71; p<0.001). Therefore, a baseline EGC that exclusively covers a period of fasting may exhibit even a larger association than the observed correlation between follow-up EGC and different glycaemic levels.

There were corroborated previous results that indicates that HbA1c levels is affected by age. HbA1c was also affected by the level of education. It is quite likely that the type of job done may explain this. It has been shown that these works that require a high educational level area also associated with increased working hours (Uehata, 1991) which, in turn, are also associated with increased $HbA_{1c}$ (Azami et al., 2018). We also verified previous results that indicate that smoking decreased FSG and PSG. By contrast, earwax was also a more stable specimen, since its cortisol levels were not affected by any covariate. Our results suggest that the next step should be start testing EGC among diabetic and obese patients.

Some previous studies have used the area under the curve, rather than the mean between fasting and postprandial glucose levels for estimating the average glucose concentration (Avignon et al., 1997). However, the mean between fasting and postprandial glycaemic levels have also shown to be a very accurate index. In fact, Svendson and coworkers found that the average glucose levels derived from approximately 2 to 300 measurements in each of 18 type 1 diabetes patients correlated almost perfectly (R=0.96) with $HbA_{1c}$ (Aaby Svendsen et al., 1982). Ozmen et al found that the mean plasma glycaemic levels derived from fasting and postprandial plasma glucose levels also correlates strongly with $HbA_{1c}$ c in Type 2 diabetic patients (Ozmen et al., 2006). Recently, the mean between postprandial and fasting glycaemic levels was also used in women with gestational diabetes mellitus (Koren et al., 2016). Therefore, this index may correlate even better with the mean glycaemic levels in healthy people, since their 24 h blood glucose levels vary less than in diabetic patients (Praet et al., 2006).

Inter-individual differences related to participants' abilities to absorb different meal components may have also an effect on their glucose levels (Freckmann et al., 2007). That is why some studies use the glucose tolerance test after the intake of 75 g of glucose, rather than postprandial levels after a standardised meal (Ensure), which contains various nutrients, such as proteins, lipids and glucose that may have different absorption rates, varying the final PSG level. However, we used a test that it is widely used, providing a liquid meal that is easy to absorb. Furthermore, there were excluded participants with food allergies, such as lactose intolerance.

With regards to the differences in blood glucose level between plasma and serum, some studies reported that plasma glucose is higher than serum glucose whereas other studies found no difference. Nonetheless, measurement of glucose in serum is not recommended for the diagnosis of diabetes (American Diabetes Association, 2010). However, we did not use FSG or PSG levels to make any diagnosis, since we recruited a sample of healthy participants to investigate their glucose levels using different specimens.

To conclude, earwax is more accurate than glycaemic and $HbA_{1c}$ specimens for reflecting the average glucose levels, because it is a more stable specimen and its glucose concentration better predicted the average glucose concentration, rather than the its fasting or postprandial levels.

Measuring Cortisol Levels Using Earwax Sample

Background: The depressive diagnostic is considered less than fully reliable. This may be explained by the large heterogeneity of this syndrome. One accurate biomarker may improve the consistency of this diagnosis. Cortisol level has normally been measured in depression, since it is a frequent neurobiological alteration in this syndrome. However, cortisol results using short-term specimens have been very diverging, due to the reactive cortisol secretion profile. These specimens are inappropriate for reflecting the average cortisol concentration, because several acute influences affect their cortisol levels. Hair Cortisol Concentration (HCC) may accurately reflect the long-term cortisol levels, because accumulates the hormone over long-periods. However, its widespread use seems unrealistic. Furthermore, it is not completely clear whether some acute influences do vary HCC. Earwax Cortisol Concentration (ECC) may be a more convenient and accurate specimen for reflecting the average cortisol concentration.

Methods: The ears of 37 healthy participants were cleaned during a baseline visit. One month after, ECC were analysed from participants' right ear. During that follow-up visit, participants also provided 1 cm of hair that represented the retrospective month of hair cortisol accumulation. ECC and HCC were compared and correlated between them.

Results: ECC was significantly larger than HCC (P<0.001). ECC and HCC showed a significant moderate positive association (R=0.39; p=0.03). While males had increased HCC than females (p<0.001), ECC was not affected by gender.

Conclusion: ECC may constitute another specimen that accurately reflects the average cortisol concentration. In comparison to hair, earwax accumulates larger cortisol concentrations. Earwax was also a more stable specimen, since its cortisol levels were not affected by any covariate. Ultimately, the time needed for analysing ECC was significantly less than the time needed for analysing HCC.

Aims & Hypothesis

Although we recently found that this hormone it is detectable in this secretion (Herane-Vives & Benohr, 2018), it is unknown whether the level found of it represented the average cortisol concentration. That is why in this study we correlated Earwax Cortisol Concentration (ECC), and HCC in a sample of 37 healthy participants. We hypothesized that: 1) The time needed for analysing ECC would be less than the time needed for analysing HCC, 2) ECC would be larger than HCC, 3) ECC and HCC would positively correlate between them and, 4) Common short-term and hair cortisol covariates would not affect ECC.

Methods

We compared and correlate the cortisol levels that were obtained from the right follow-up earwax sample and form one hair sample of 1 cm that was obtained also during the same visit. Both samples represented the retrospective month of cortisol accumulation. The effect of several covariates was investigated in these samples. The time needed for analysing ECC was also recorded.

Earwax Sample Using Trears (see diagram 1 of instructions)

Earwax Cortisol Analysis

Purification of Cortisol from earwax: After obtaining the earwax samples by TEARS® device, the samples resuspended in 500 µl of PBS were homogenized using a 1 ml syringe. Then, 500 µl of diethyl ether was added and each of the samples was stirred for 1 minute using a vortex, and then left at −20° C. for 2 hours. After that time, the liquid fraction of each of the samples (organic fraction) was transferred to a new 5 ml tube properly labeled and dried using the $N_2$ displacement method described above. Once dried, the samples were resuspended in 500 µl of PBS and Cortisol levels were quantified. On the other hand, the aqueous fraction that remained after extraction with diethyl ether was used to quantify glucose levels in cerumen.

Quantification of Cortisol from earwax samples: The amount of cortisol was quantified by the use of ELISA, according to the instructions given by its suppliers (Enzo Life Sciences, Farmingdale, NY, USA). The amount of cortisol was quantified by competitive colorimetric ELISA techniques, using a standard curve of 0, 156, 313, 625, 1250, 2500, 5000 and 10000 pg/ml of Cortisol Standard. 100 µl of standard solutions, organic sample fractions and dilutions of sera were added to the wells of a plate coated with an anti-mouse antibody. In addition to the solutions mentioned above, 50 µl of a blue conjugate containing Cortisol covalently bound to an alkaline phosphatase and 50 µl of a mouse monoclonal antibody against Cortisol are added to all wells. Once the antibody is added, they are incubated for 2 hours with agitation, in order to make the cortisol present in the samples/standards compete with the cortisol of the conjugate with the antibody against the hormone and this antibody will remain bound to the well by its interaction with the antibody. the secondary antibody adhered to the walls of the wells. After 2 hours, the wells are thoroughly washed and 200 µl of para-nitrophenyl-phosphate (pNpp) were added to each well and incubated for 1 hour without agitation. This is so that the para-nitrophenyl phosphate is transformed by an enzymatic reaction mediated by alkaline phosphatase covalently linked to cortisol in para-nitro phenol and of a coloration inversely proportional to the amount of cortisol present. Finally, 50 µl of a solution for stopping the enzymatic reaction were added to each well. The plate is read at 405 nm in a microplate reader (NovoStar), the absorbance of the standard curve is adjusted to a 4-point logistic curve and the absorbances of the samples are interpolated in said curve, obtaining the concentration of the samples in pg/ml. For the calculation of the pg/mg of cerumen, the concentration is multiplied by the µl of sample (500 µl) and divided by the weight of the dry sample. To calculate the concentration in serum, it was multiplied the concentration by the dilution factor.

Hair Samples

A trained clinician collected hair samples of all participants. The presence and frequency of any biological confounders and procedures potentially affecting hair cortisol levels were measured, including cosmetic treatments (dyeing, bleaching, permanent straightening or waving) and frequency of hair washing. Hair samples were taken from the vertex at the back of the head and were cut with cleaned scissors as close to the scalp as possible. For this study, four locks of hair were required from different places from the vertex posterior, each to be the approximate thickness of a rubber band of 1 centimetre. At the laboratory, 1 cm of hair measured from the end to the scalp surface were cut from each lock, representing approximately 1 month of hair growth equivalent to 1-month retrospective assessment of cortisol production. The total weight of the four 1 cm segments from each lock is approximately equivalent to 25-50 mg of hair. Once collected, hair samples were stored at room temperature in the dark in a sealed container.

Hair Cortisol Analysis

Prior to analysis, the hair samples were washed in 1 ml of isopropanol to remove external contaminants, the isopropanol was removed from the vial and the hair allowed to dry in a clean air environment for 48 hours. Once fully dry five ceramic balls were added to each tube and the hair samples ground to a powder using am MPbio Fast Prep (MP Biomedicals, LLC). To extract cortisol, 1.75 ml of methanol was added to each sample and the samples incubated for 20 hours whilst rotating the samples constantly.

The hair, methanol and ceramic balls were decanted into a polypropylene tube (Sarstedt AG & Co, Germany) that separated the ceramic balls from the rest of the mixture. The tube was centrifuged at 3000 RCF to separate the ground hair and methanol and 1.25 ml of the clear methanol supernatant was decanted into a 2 ml polypropylene cryovial. The methanol was then removed using a vacuum centrifuge (Scan Speed 40, Labgene) and the tubes frozen at −80° C. until required for the cortisol ELISA. Cortisol levels were determined using a commercially available competitive ELISA (Salimetrics LLC, USA). Samples were thawed and reconstituted with 0.125 ml of Salimetrics cortisol assay diluent and the samples were then assayed in accordance with the manufacturer's protocol. The results were expressed as picograms of cortisol per milligram of hair. All hair samples were analysed at Biomarker Analysis Laboratory at Anglia Ruskin University, Cambridge, UK (www.anglia.ac.uk)(Albermann & Musshoff, 2012).

Statistical Analysis

The data was checked for normality using the Kolmogorov-Smirnov statistical test and graphic methods, such as histograms; ECC and HCC values were normally distributed. Therefore, we used the (dependent t-test) for dependent samples for comparing ECC and HCC. Pearson correlations was used to determine the association between HCC and ECC. Cohen's criteria for correlations were used: low when r=0.1–0.3, moderate when r=0.3–0.5 and high when r=0.5–1.0 (J Cohen, 2013). Linear regression analysis was used to determine the association between glucose concentration and different biological and psychological variables. The time needed for analysing ECC was also recorded. The level of significance was set at $p \leq 0.05$ (two-tailed).

Results

Figure 13:
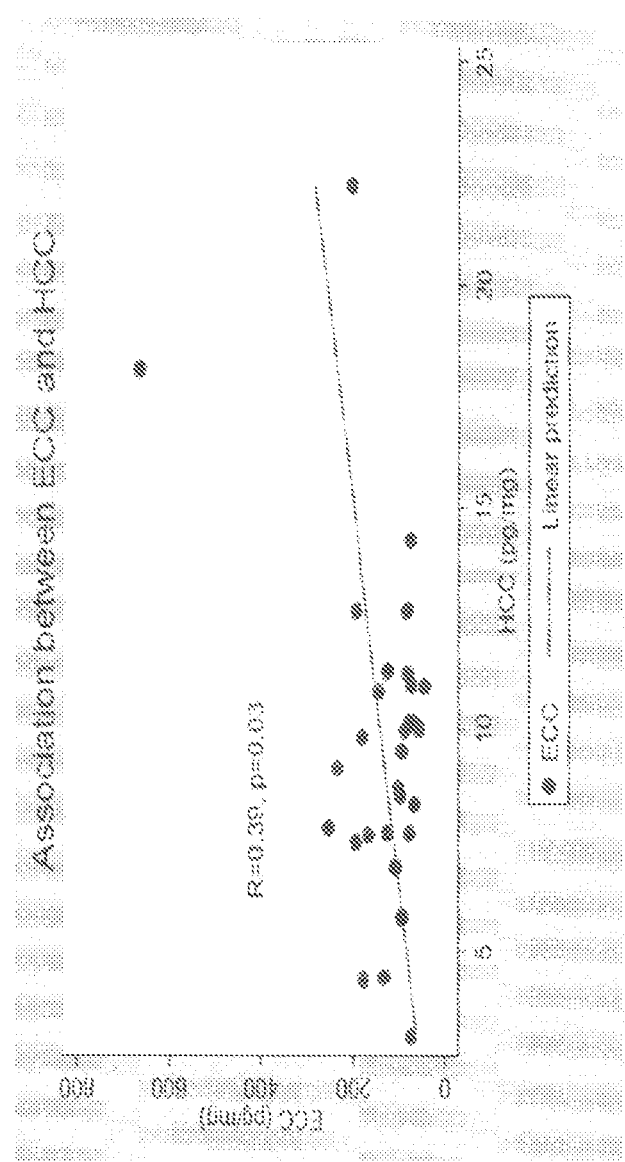
FIG. 13 is a graph showing the results of the association between HCC and ECC

Detailed socio-demographic, anthropometric and self-administrated questionnaire results can be found in table III.1, III.2 and III.3, respectively. The time needed for analying ECC using Trears was a half than the time needed for analysing ECC using the Alexander-Reiner syringe (compare tables II.4 and VI.1). The time needed for analysing ECC using Trears was more than 4 times less that the time needed for analysing HCC (Table VI.1). ECC was significantly larger than HCC (Table VI.2). While males had increased HCC in comparison to females (P<0.001) (table VI.3), gender did not affect ECC. ECC showed a moderate positive correlation with HCC (R=0.39, p=0.003) (FIG. 13)

TABLE VI.1

Time needed to analyse ECC
Quantification time

| PROCESS | Cortisol using TEARS | PROCESS | Hair* |
|---|---|---|---|
| Centrifugation of the sample | 00:00 | Technical Time | 0:26 |
| Drying of the sample with N$_2$ prior to extraction | 00:47 | incubation | 24:00 |
| Extraction of the sample with organic solvent | 02:10 | Rotating evaporator Time | 3:00 |
| Drying of the sample after extraction | 00:40 | Total, Processing Time | 27:26 |
| Quantification protocol Technical time (Hours) | 04:00 | | 0:06 |

TABLE VI.1-continued

Time needed to analyse ECC
Quantification time

| PROCESS | Cortisol using TEARS | PROCESS | Hair* |
|---|---|---|---|
| | | Centrifugation | 0:25 |
| | | Robot Time | 4:00 |
| | | Total, analysis | 4:31 |
| TOTAL TIME 07:37 | | | 31:57 |

*These values were obtained thanks to the courtesy of Bristow, M. BIOMARKER ANALYSIS LABORATORY QUOTATION AT ANGLIA RUSKIN ENTERPRISE (2017), Cambridge.

TABLE VI.2

HCC and ECC comparisons

| ECC (pg./mg) | | | | HCC (pg./mg) | | | | |
|---|---|---|---|---|---|---|---|---|
| Q1 | Median | Mean | Q3 | Q1 | Median | Mean | Q3 | P-value |
| 79.8 | 124.7 | 137.8; (20.8) | 200.3 | 7.6 | 9.7 | 9.7 (0.7) | 10.9 | <0.001* |

ECC: Earwax Cortisol Concentration;
HCC: Hair Cortisol Concentration
*P-value significant at 0.05

TABLE VI.3

Linear regression model between covariates and HCC and between covariates and ECC

| | ECC (pg./mg) | | | HCC (pg./mg) | | |
|---|---|---|---|---|---|---|
| Variables | β | p-value | CI | β | p-value | CI |
| Age | 0.6 | 0.78 | −3.8 | 0.1 | 0.48 | −0.1; 0.2 |
| Sex | 53.8 | 0.14 | −19.0; 126.7 | 3.7 | <0.001* | 1.1; 6.3 |
| Alcohol (unit)* | −2.3 | 0.73 | −16.0; 11.4 | 0.1 | 0.60 | −0.4; 0.6 |
| Tobacco | −26.0 | 0.54 | −112.5; 60.8 | 3.0 | 0.06 | −0.2; 6.3 |
| BMI (Kg/cm$^2$) | 4.3 | 0.37 | −5.4; 14.0 | 0.3 | 0.12 | −0.1; 0.7 |
| Waist circumference (cm) | 0.8 | 0.53 | −1.8; 3.4 | 0.1 | 0.17 | <−0.1, 0.2 |
| Anti-conceptive pill | −8.6 | 0.62 | −87.8; 70.6 | <0.1 | 0.96 | −2.8; 2.9 |
| Hair washing | 15.1 | 0.19 | −7.9; 38.1 | 0.6 | 0.15 | −0.2; 1.5 |
| Cosmetic treatment | 81.4 | 0.47 | 147.9; 310.7 | −6.3 | 0.87 | −8.8; 7.5 |
| PSS | −1.0 | 0.72 | −6.9; 4.8 | <−0.1 | 0.96 | −0.3; 0.2 |
| Number of Hassles | <0.2 | 0.91 | −3.8; 3.4 | <−0.1 | 0.60 | <0.2; 0.1 |
| Severity of Hassles | −0.6 | 0.58 | −2.7; 1.6 | <−0.1 | 0.78 | −0.1; 0.1 |
| RLCQ | −0.1 | 0.51 | −0.4; 0.2 | <−0.1 | 0.68 | <−0.1; <0.1 |

TABLE VI.3-continued

Linear regression model between covariates and HCC and between covariates and ECC

| Variables | ECC (pg./mg) | | | HCC (pg./mg) | | |
| --- | --- | --- | --- | --- | --- | --- |
| | β | p-value | CI | β | p-value | CI |
| Severe RLCQ | −17.5 | 0.43 | −62.7; 27.6 | <−0.1 | 0.96 | −1.7; 1.7 |

PSS: Perceived Stress Scale.
RLCQ: Recent Life Event Questionnaire.
One alcohol unit is measured as 10 ml or 8 g of pure alcohol. This equals one 25 ml single measure of whisky (Alcohol by volume (ABV) 40%, or a third of a pint of beer (ABV 5-6%) or half a standard (175 ml) glass of red wine (ABV 12%). In comparison to under or postgraduate studies.

Please see FIG. 13.

Discussion

ECC using Trears was significantly more efficient than using the Alexader-Reiner syringe. That performance is even better if we compare the time needed for analysing HCC. Earwax concentrated significantly more cortisol concentration than hair. Earwax is also a more stable specimen than hair for reflecting cortisol levels, since, it was not by any covariate. Indeed we corroborated previous studies that indicate that males have increased HCC in comparison to females (Garcia-Leon et al., 2018; Vanaelst et al., 2012).

Hair is another specimen able to accumulate cortisol concentration since it showed a positive correlation with one specimen that has already been validated for measuring long-term cortisol levels. This property was reinforced after observing that this novel specimen was not affected by any acute influences. ECC may show an increased correlation with 24 h urine collection or with continuous cortisol levels, since some evidence suggest that HCC is affected by acute influenced acute influences, such as sweat (Sharpley, 2012) and nerve fibres (Okumura, 1967).

Earwax accumulates larger cortison concentration than hair. Cortisol is indirectly delivered into the hair shaft by one unclear multi-compartment model compartment model. However, cortisol is directly secreted into the external auditory canal by the one simple single-compartment model, given by the ceruminous glands. One potential limitation is related to ECC/HCC comparisons. Although this study used the same sample of participants, their results were not strictly comparable because these specimens were analysed in two different laboratories. Clark et al., (1998) showed, for instance a significant bias ratios of up to 1.2 between five different immunoassays in controls undergoing a standard corticotrophin test (Jeremy Cohen et al., 2006). However, we found a ECC/HCC ratio up to 14.3. Apart from that extremely large fraction, both laboratories used ELISA techniques. Thus, it is extremely unlikely that difference had been found by chance. Future studies may correlate ECC with fingernail cortisol levels, another specimen that may aggregate cortisol levels over long-term (Izawa et al., 2015). Ultimately, ECC should be measured among depressive patients.

Conclusion

Trears may constitute a more economical, convenient and effective method for self-cleaning outer ears in healthy people. This device may also replace the use of current risky cotton swabs. Earwax samples accurately reflects an average of cortisol and glucose levels. Common acute influences do not affect glucose and cortisol earwax levels.

The invention claimed is:

1. A method for measuring glucose and cortisol levels in earwax comprising the steps of:
   extracting earwax samples from the ear;
   preparing the extracted earwax samples for purposes of measuring cortisol and glucose levels in the samples;
   measuring cortisol and glucose levels in the extracted earwax samples; wherein:
   the extraction of at least one earwax sample is carried out by means of an extraction device comprising:
   a handle having a first end and a second end,
   a sponge head comprising a base and a longitudinally extending elongated member directly depending from an upper portion of the base, wherein a lower portion of the base is removably coupled to the second end of the handle and wherein the elongated member has a star shaped cross section, and
   an elongated sponge having a centrally located longitudinal receiving area in which the elongated member of the base is removably received, and
   wherein the extracted earwax sample is obtained by inserting the elongated sponge of the extraction device into the ear canal,
   wherein the preparation of the extracted earwax sample is carried out by:
   adding a Phosphate Buffered Saline buffer solution to a tube;
   separating the sponge from the sponge head and introducing it into the tube,
   after the sponge has absorbed the entire solution, repeatedly squeezing the sponge to expel the absorbed buffer solution and then allowing the sponge to reabsorb the expelled buffer solution,
   squeezing the sponge dry and removing it from the tube;
   drying the resulting solution;
   resuspending the resulting content in ultrapure water; and
   storing the resulting solution until use, and
   wherein the cortisol levels are measured by means of ELISA techniques and the glucose levels are measured by using a kit for determining glucose levels from the dissolved earwax solution.

2. A method for measuring glucose and cortisol levels as claimed in claim 1, wherein:
   a preparation of the one or more samples is carried out by:
   (a) drying the each of the one or more earwax samples until all water is evaporated from each sample through baking lyophilization or using an $N_2$ stream at ambient temperature so as to produce one or more dry earwax samples, (b) weighing each of the one or more dry earwax samples so that the amount of cortisol may be normalized on a dry weight basis such that the measured weight is adjusted to a common scale in order to be able to compare the data;

(c) homogenizing the one or more dry samples with a Phosphate Buffered Saline solution in order to obtain a solution in which earwax is dissolved;

(d) dividing the solution obtained in step c) into a first solution portion, and a second solution portion and adding each solution portion to a first and second sample container, respectively, (e) adding a solvent to the first solution portion in a relation of 1:1 between the PBS and the first solution portion in order to obtain a solution of earwax in PBS mixed with solvent;

(f) agitating the tube containing the solution obtained in step e) during a period of time of at least one minute and adding 0.5 mg of diethyl-ether the relation with PBS being 1:1;

(g) cooling the mixed solution obtained in step f) at a temperature of −18 to −21° C. during a period of time of at least two hours in order to be sure that the Phosphate Buffered Saline part of the mixed solution is frozen and it does not contaminate the organic diethyl-ether fraction;

(h) extracting from the cooled solution obtained in step g) the compounds which are specifically solubilized in diethyl-ether;

(i) drying the remaining fraction of liquid solution obtained in step g);

(j) storing the dried fraction obtained in step i) at −80° C. for further use;

(k) adding 300 pg of cortisol to the second solution portion in order to obtain a solution of earwax in PBS mixed with cortisol;

(l) adding 0.5 ml of a solvent to the solution obtained in step k) in order to quantify the amount of purified cortisol;

(m) agitating the second container containing the solution obtained in step l) during a period of time of a least one minute in order to mix the solution and then adding 0.5 mg of diethyl-ether the relation with PBS being 1:1;

(n) cooling the mixed solution obtained in step m) at a temperature of −18 to −21° C., during a period of time of at least two hours in order to be sure that the Phosphate Buffered Saline part is frozen, and it does not contaminate the organic diethyl-ether fraction;

(o) extracting from the cooled solution obtained in step n) the compounds which are specifically solubilized in diethyl-either;

(p) drying the remaining fraction of liquid solution obtained in step n);

(q) storing the dried fraction obtained in step i) at a temperature of between about −20 to −90° C. for further use;

(r) dissolving 0.5 ml of 300 pg/ml of purified cortisol solution in PBS at a pH of between about 6.8 and 7.2;

(s) carrying out the same procedure to extract cortisol from the first solution portion and the second solution portion;

(t) the cortisol measurement is carried out by:

(a) reconstituting the extracted samples using a buffer assay given by the manufacturer, which allows the quantification of cortisol, using colorimetric competitive ELISA techniques by adding the buffer to the extracted samples for obtaining a solution, letting the solution rest and then agitating the solution, (b) using a standardized curve for cortisol levels to measure the total amount of cortisol in the sample;

(c) normalizing the quantified amount by dry grams of ear-wax using fluorometric techniques in which the fluorometer is excited within a range of 530-570 nm and read within a range of emission of 590-600 nm and the glucose measurement is carried out using a kit for determining glucose levels from the dissolved ear-wax solution, wherein glucose absorption is quantified in triplicate at 505 nm and glucose concentration (mg/dl) is obtained using its absorption averages, and the total amount of glucose in the dissolved solution is calculated according to the initial weight of the samples after a process of normalization.

3. A method for measuring glucose and cortisol levels as claimed in claim 2, wherein step e) the solvent comprises diethyl ether.

4. A method for measuring glucose and cortisol levels as claimed in claim 2, wherein in step i) the remaining fraction of liquid solution is dried by means of a $N_2$ steam at ambient temperature.

5. A method for measuring glucose and cortisol levels as claimed in claim 2, wherein in step I) the solvent comprises diethyl ether.

6. A method for measuring glucose and cortisol levels as claimed in claim 2, wherein in step p) the remaining fraction of liquid solution is dried by means of a $N_2$ steam at ambient temperature.

7. A method for measuring glucose and cortisol levels as claimed in claim 1, wherein in the preparation of the sample the proportion between weight of sponge and volume of PBS is 1:2.

8. A method for measuring glucose and cortisol levels as claimed in claim 1, wherein in the preparation of the sample the resulting solution is dried by displacement with $N_2$.

9. A method for measuring glucose and cortisol levels as claimed in claim 1, wherein in the preparation of the sample the resulting solution is stored at 4° C.

* * * * *